United States Patent
Zhang et al.

(10) Patent No.: US 12,312,324 B2
(45) Date of Patent: May 27, 2025

(54) FLUORINE-CONTAINING SUBSTITUTED BENZOTHIOPHENE COMPOUND, AND PHARMACEUTICAL COMPOSITION AND APPLICATION THEREOF

(71) Applicant: Shanghai Institute of Materia Medica, Chinese Academy of Sciences, Shanghai (CN)

(72) Inventors: Ao Zhang, Shanghai (CN); Meiyu Geng, Shanghai (CN); Chunyong Ding, Shanghai (CN); Zuoquan Xie, Shanghai (CN); Jian Ding, Shanghai (CN); Yan Zhang, Shanghai (CN); Ancheng Shen, Shanghai (CN); Xiyuan Wang, Shanghai (CN)

(73) Assignee: SHANGHAI INSTITUTE OF MATERIA MEDICA, CHINESE ACADEMY OF SCIENCES, Shanghai (CN)

( * ) Notice: Subject to any disclaimer, the term of this patent is extended or adjusted under 35 U.S.C. 154(b) by 901 days.

(21) Appl. No.: 17/420,389

(22) PCT Filed: Dec. 31, 2019

(86) PCT No.: PCT/CN2019/130605
§ 371 (c)(1),
(2) Date: Jul. 1, 2021

(87) PCT Pub. No.: WO2020/140894
PCT Pub. Date: Jul. 9, 2020

(65) Prior Publication Data
US 2022/0089561 A1    Mar. 24, 2022

(30) Foreign Application Priority Data

Jan. 2, 2019   (CN) .......................... 201910002749.2

(51) Int. Cl.
*C07D 333/64* (2006.01)
*C07D 409/12* (2006.01)

(52) U.S. Cl.
CPC ......... *C07D 333/64* (2013.01); *C07D 409/12* (2013.01)

(58) Field of Classification Search
CPC .. C07D 333/64; C07D 409/12; A61K 31/381; C08G 2261/3243
See application file for complete search history.

(56) References Cited

U.S. PATENT DOCUMENTS 4,212,815 A  *  7/1980  Boswell, Jr. ............ C07C 45/63
                                                    552/502
2018/0093964 A1*  4/2018  Altman ................... A61P 37/00

FOREIGN PATENT DOCUMENTS

| TW | 201605790 A | 2/2016 |
| WO | 2005077926 A2 | 8/2005 |
| WO | 2006115845 A1 | 11/2006 |
| WO | 2018067423 A1 | 4/2018 |
| WO | 2019195124 A1 | 10/2019 |

OTHER PUBLICATIONS

Valeur, Eric; Bradley, Mark, Amide Bond Formation: Beyond the Myth of Coupling Reagents, Dec. 4, 2008, Chemical Society Reviews, 38, pp. 606-631 (Year: 2008).*
STN Record for CAS 2228391-58-8 (Year: 2018).*
Valeur et al, Amide Bond Formation: Beyond the Myth of Coupling Reagents, Chemical Society Reviews, Dec. 4, 2008 (Year: 2008).*
Meanwell, Fluorine and Fluorinated Motifs in the Design and Application of Bioisosteres for Drug Design, J. Med. Chem. 2018, 61, 5822-5880 (Year: 2018).*
Ballatore et al, Carboxylic Acid (Bio)Isosteres in Drug Design, ChemMedChem, 2013, 8, 385-395 (Year: 2013).*
Int'l Search Report issued Apr. 7, 2020 in Int'l Application No. PCT/CN2019/130605.
"Stn Regisrty" RN: 2228391-58-8, Jun. 28, 2018 (Jun. 28, 2018).

* cited by examiner

*Primary Examiner* — Noble E Jarrell
*Assistant Examiner* — Phillip Matthew Rzeczycki
(74) *Attorney, Agent, or Firm* — Panitch Schwarze Belisario & Nadel LLP

(57) ABSTRACT

A fluorine-containing substituted benzothiophene compound and a pharmaceutical composition and an application thereof are described. The compound has the structure as shown in formula (I), in which the definitions of each group and substituent are as described in the description. A preparation method of the compound and an anti-tumor application thereof are also described.

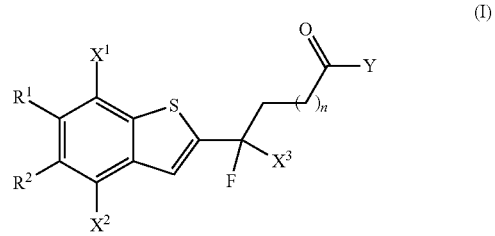

10 Claims, No Drawings

FLUORINE-CONTAINING SUBSTITUTED BENZOTHIOPHENE COMPOUND, AND PHARMACEUTICAL COMPOSITION AND APPLICATION THEREOF

CROSS-REFERENCE TO RELATED APPLICATIONS

This application is a Section 371 of International Application No. PCT/CN2019/130605, filed Dec. 31, 2019, which was published in the Chinese language on Jul. 9, 2020 under International Publication No. WO 2020/140894 A1, which claims priority under 35 U.S.C. § 119 (b) to Chinese Application No. 201910002749.2, filed on Jan. 2, 2019, the disclosures of which are incorporated herein by reference in their entireties.

TECHNICAL FIELD

The present invention relates to the field of medicine, and more particularly to a type of fluorine-containing substituted benzothiophene compound and a pharmaceutical composition and application thereof.

BACKGROUND ART

As a regulator of cytokine signaling pathways, interferon gene stimulating protein is closely related to the pathology and clinical symptoms of a variety of diseases, including infectious diseases, cancer and autoimmune diseases. The protein is a transmembrane protein, which usually connects to form a dimer in 152-173 dimerization domain and is in a self-inhibiting state. When stimulated by partial ligands such as cyclic dinucleotides, the molecular configuration changes and is activated, recruiting TANK-binding kinase 1 (TBK1) in the cytoplasm, and mediating the phosphate of TBK1 to IRF3, which leads to the formation of interferon (IFN)-β and many other cytokines, and through a series of cascade reactions, the adaptive immune system was activated to activate T cells. Under normal circumstances, the normal activity of the interferon gene stimulating protein maintains the normal function of the immune system, the lack of its activity leads to immune deficiency, and the over-activation can lead to immune hyperactivity.

Tumor microenvironment (TME) innate immune signaling is a key step in the activation of tumor-specific T cells and the infiltration of tumor infiltrating lymphocytes (TIL). Among them, type I IFN plays a key role in tumor-activated T cell activation. STING agonist not only induces the expression of type I interferon genes, but also plays an important role in natural immune signaling pathways. It can also activate immune stimulating cells including dendritic cells, change the tumor microenvironment and induce the production of tumor-specific T cells, thereby killing tumor cells.

The normal activation of cyclic guanylate-adenylate synthase (cGAS)/STING signaling pathway can not only induce the production of cytokines and activate tumor-targeting T cells, but also trigger the body's immune response to tumor cells, thereby enhancing the curative effect of tumors radiotherapy. For example, cGAS can sense the DNA released by killed tumor cells to activate STING to induce dendritic cells to produce type I interferon, which in turn activates the potential anti-tumor immune response and enhances the efficacy of radiotherapy.

Interferon gene stimulating protein agonists show certain potential in combination with other immune checkpoint inhibitors. Although two monoclonal antibody drugs have been successfully marketed for immune checkpoint PD-1/PD-L1, the overall efficiency of these drugs is relatively low, only about 20-30%. PD-1/L1 inhibitors can relieve the inhibition of T cell activation, but if there are no T cells inside/near the tumor, it is difficult for such drugs to exert efficacy, which is part of the reason for the low overall efficiency of such drugs. Thus, patients need to have an immune response before using this type of drug, so that checkpoint suppression can work. The inherent immune system is capable of completing this task. Thus, activated interferon gene stimulating proteins can provide a basis for the activation and proliferation of T cells, and then a checkpoint inhibitor can be used to make T cells have sufficient ability to remove tumor cells in vivo.

In summary, activated interferon gene stimulating protein which induces the production of type I interferon has become a promising research direction in the field of anti-tumor immunity. The interferon gene-stimulating protein agonists that have been reported to be effective against both human and murine sources are mainly cyclic dinucleotide (CDN) compounds, such as ADU-S100, MK-1454, etc., which have entered phase I clinical studies, but such compounds are complex in structure and difficult to synthesize. More importantly, they have disadvantages such as unstable metabolism and high adverse reaction rate. As a result, the current drug administration method is mainly intratumor injection, which greatly limits its clinical application.

Therefore, it is necessary to further develop new small molecules with simple structure, convenient synthesis, stable metabolism and high safety to activate the interferon gene stimulating protein and induce the production of type I interferon IFN-β.

SUMMARY OF THE INVENTION

The purpose of the present invention is to provide a compound represented by formula I, a preparation method thereof, and its use in anti-tumor.

In the first aspect of the invention, a compound of formula I, or its isomer, prodrug, solvate, hydrate or pharmaceutically acceptable salt thereof is provided,

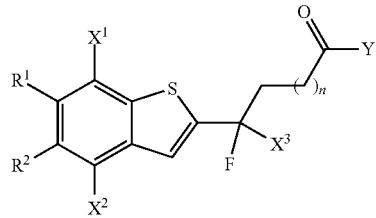

Formula I wherein, $R^1$ and $R^2$ are independently selected from the substituted or unsubstituted group consisting of H, halogen, amino, hydroxyl, carboxyl, C1-C6 alkyl, C2-C6 alkenyl, C2-C6 alkynyl, C3-C8 cycloalkyl, C1-C6 alkoxy, C3-C8 cycloalkoxy, 3-8 membered heterocycloalkyl containing 1 to 3 heteroatoms selected from N, O or S, 3-8 membered heterocycloalkoxy containing 1 to 3 heteroatoms selected from N, O or S, C6-C10 aryl, and 3-10 membered heteroaryl containing 1 to 3 heteroatoms selected from N, O or S; or $R^1$ and $R^2$ together with the carbon atoms to which they are attached form a 5-14 membered heterocyclic group;

the substituted in $R^1$ and $R^2$ refers to be independently substituted by one or more substituents selected from the group consisting of halogen, amino, hydroxy, carboxy, C1-C6 alkyl, C3-C8 cycloalkyl, C1-C6 alkoxy, C3-C8 cycloalkoxy, 3-8 membered heterocyclic group containing 1 to 3 heteroatoms selected from N, O or S, C6-C10 aryl, and 3-10 membered heteroaryl containing 1 to 3 heteroatoms selected from N, O or S;

$X^1$ and $X^2$ are independently selected from the group consisting of H, D, halogen, unsubstituted or halogen-substituted C1-C6 alkyl, unsubstituted or halogen-substituted C1-C6 alkoxy, and cyano;

$X^3$ is selected from the group consisting of hydrogen, halogen, hydroxy, C1-C3 alkyl, C1-C3 alkoxy;

n is an integer selected from 0, 1, 2, 3, 4, 5, 6, 7 or 8;

Y is selected from the group consisting of —$OR^3$, and —$N(X^4R^4)R^5$, wherein, $X^4$ is selected from the group consisting of O, S, and NH;

$R^3$ is selected from the substituted or unsubstituted group consisting of H, carboxy, sulfonic acid group, phosphoryl group, C1-C6 alkyl, C3-C8 cycloalkyl, C6-C10 aryl, 3-10 membered heteroaryl containing 1 to 3 heteroatoms selected from N, O or S, and 3-8 membered heterocycloalkyl containing 1 to 3 heteroatoms selected from N, O or S;

$R^4$ and $R^5$ are independently selected from substituted or unsubstituted the group consisting of H, carboxy, sulfonic acid group, phosphoryl group. C1-C6 alkyl. C2-C6 alkenyl, C2-C6 alkynyl, C3-C8 cycloalkyl, C1-C6 alkoxy, C3-C8 cycloalkoxy, C6-C10 aryloxy, C6-C10 aryl, 3-8 membered heterocycloalkyl containing 1 to 3 heteroatoms selected from N, O or S, and 3-10 membered heteroaryl containing 1 to 3 heteroatoms selected from N, O or S;

the substituted in $R^3$, $R^4$ and $R^5$ refers to be independently substituted by one or more substituents selected from the group consisting of halogen, hydroxyl, amino, carboxyl, C1-C6 alkyl, C3-C8 cycloalkyl, C1-C6 alkoxy, C3-C8 cycloalkoxy, 3-8 membered heterocyclic group containing 1 to 3 heteroatoms selected from N, O or S, C6-C10 aryl, and 3-10 membered heteroaryl containing 1 to 3 heteroatoms selected from N, O or S.

In another preferred embodiment, when $R_1$ and $R_2$ together with the carbon atoms to which they are connected form a 5-14 membered heterocyclic group, the 5-14 membered heterocyclic group is a heterocyclic group containing 1-4 O, preferably a heterocyclic group containing 2 O.

In another preferred embodiment, the 5-14 membered heterocyclic group is a cycloalkoxy containing 2 O.

In another preferred embodiment, $X^3$ is halogen.

In another preferred embodiment, $X^3$ is fluorine.

In another preferred embodiment, $X^2$ is hydrogen or fluorine.

In another preferred embodiment, n is an integer selected from 0, 1 or 2.

In another preferred embodiment, Y is selected from the group consisting of —$OR^3$, and —N $(X^4R^4)R^5$, wherein, $X^4$ is selected from the group consisting of: O, and NH;

$R^3$ is selected from the substituted or unsubstituted group consisting of H, carboxy, sulfonic acid group, phosphoryl group, C1-C6 alkyl, C3-C8 cycloalkyl, C6-C10 aryl, 3-10 membered heteroaryl containing 1 to 3 heteroatoms selected from N, O or S, and 3-8 membered heterocycloalkyl containing 1 to 3 heteroatoms selected from N, O or S:

$R^4$ and $R^5$ are independently selected from the substituted or unsubstituted group consisting of H, carboxy, sulfonic acid group, phosphoryl group, C1-C6 alkyl, C2-C6 alkenyl, C2-C6 alkynyl, C3-C8 cycloalkyl, C1-C6 alkoxy, C3-C8 cycloalkoxy, C6-C10 aryloxy, C6-C10 aryl, 3-8 membered heterocycloalkyl containing 1 to 3 heteroatoms selected from N, O or S, and 3-10 membered heteroaryl containing 1 to 3 heteroatoms selected from N, O or S;

the substituted in $R^3$, $R^4$ and $R^3$ refers to be independently substituted by one or more substituents selected from the group consisting of halogen, hydroxyl, amino, carboxyl, C1-C6 alkyl, C3-C8 cycloalkyl, C1-C6 alkoxy, C3-C8 cycloalkoxy, 3-8 membered heterocyclic group containing 1 to 3 heteroatoms selected from N, O or S, C6-C10 aryl, and 3-10 membered heteroaryl containing 1 to 3 heteroatoms selected from N, O or S.

In another preferred embodiment, the compound is selected from the compounds listed in Table 1.

In the second aspect of the invention, a method for preparing the compound, or its isomer, prodrug, solvate, hydrate, or pharmaceutically acceptable salt thereof according to the first aspect of the present invention is provided, said method is selected from the group consisting of:

Method 1:

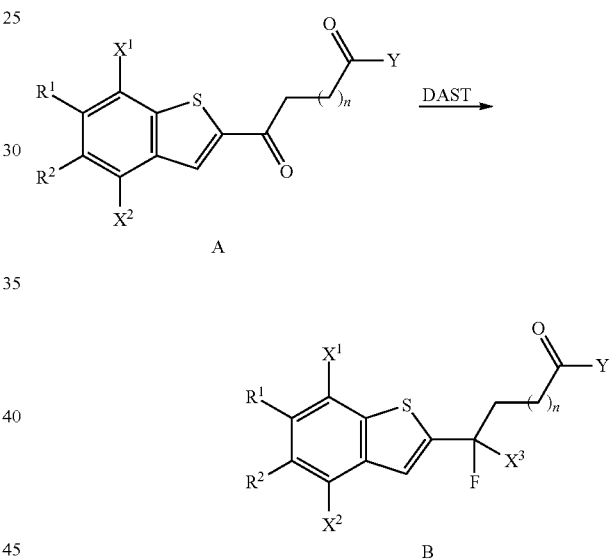

a compound of formula A is reacted with DAST to obtain B;

wherein, $R^1$, $R^2$, $X^1$, $X^2$, n, Y, and $X^3$ are as defined in the first aspect of the invention;

Method 2:

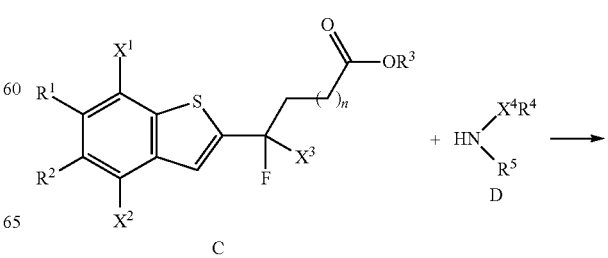

-continued

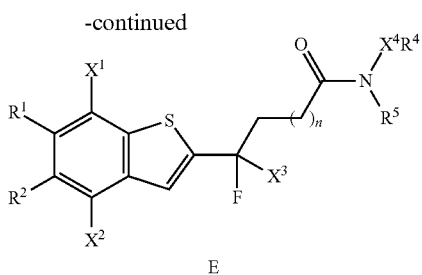

E a compound of formula C is reacted with a compound of formula D or a hydrochloride thereof to obtain E, wherein, $R^1$, $R^2$, $X^1$, $X^2$, $X^3$, n, $R^3$, $X^4$, $R^4$ and $R^5$ are as defined in the first aspect of the invention.

In another preferred embodiment, in Method 1, the compound of formula A is subjected to reduction treatment before reacting with the DAST.

In another preferred embodiment, the reduction treatment refers to the carbonyl group which is attached to the benzothiophene structure is reduced into a hydroxyl in the compound of formula A.

In the third aspect of the invention, a pharmaceutical composition is provided, comprising:

(i) one or more therapeutically effective amount of the compound, or isomer, prodrug, solvate, hydrate or pharmaceutically acceptable salt thereof according to the first aspect of the invention; and (ii) a pharmaceutically acceptable carrier.

In another preferred embodiment, the pharmaceutical composition is an injection, capsule, tablet, pill, powder or granule.

In another preferred embodiment, the pharmaceutical composition further comprises one or more second therapeutic agents, the second therapeutic agent is a drug for preventing and/or treating cancer.

In another preferred embodiment, the second therapeutic agent is a conventional cytotoxic chemotherapy drug or other anti-tumor immune drug.

In the fourth aspect of the invention, a use of the compound, or isomer, prodrug, solvate, hydrate or pharmaceutically acceptable salt thereof according to the first aspect of the invention or the pharmaceutical composition according to the third aspect of the invention for preparing preparations for preventing and/or treating diseases related to type I interferon is provided.

In another preferred embodiment, the type I interferon is IFN-β.

In another preferred embodiment, the disease related to type I interferon is selected from the group consisting of infectious disease, cancer, and autoimmune disease.

In another preferred embodiment, the cancer is selected from the group consisting of breast cancer, ovarian cancer, liver cancer, melanoma, prostate cancer, colon cancer, gastric cancer.

In the fifth aspect of the invention, an interferon gene stimulating protein agonist which comprises one or more of the compound, or isomer, prodrug, solvate, hydrate or pharmaceutically acceptable salt thereof according to the first aspect of the present invention is provided.

In the sixth aspect of the invention, a method for preventing and/or treating a disease related to type I interferon is provided, and the method comprises the step of: administrating a therapeutically effective amount of one or more of the compound, or isomer, prodrug, solvate, hydrate or pharmaceutically acceptable salt thereof according to the first aspect of the invention or the pharmaceutical composition according to the third aspect of the invention to a subject in need thereof.

It should be understood that in the present invention, any of the technical features specifically described above and below (such as in the Examples) can be combined with each other, which will not redundantly be described one by one herein.

DETAILED DESCRIPTION OF THE INVENTION

Through long and intensive research, the inventors have unexpectedly prepared a compound shown in formula I with simple structure, convenient synthesis, stable metabolism and high safety. The compound has excellent activating performance on interferon gene stimulating protein, thereby activating T cells and significantly promoting the expression of interferon factor IFN-β, thus achieving effective treatment of tumors and their complications. On this basis, the inventors have completed the present invention.

Terms

In the present invention, unless specifically indicated, the terms used have the general meaning well known to those skilled in the art.

In the present invention, the term "halogen" refers to F, Cl, Br or I.

In the present invention, "C1-C6 alkyl" refers to a straight or branched alkyl including 1-6 carbon atom, such as methyl, ethyl, propyl, isopropyl, butyl, isobutyl, sec-butyl, tert-butyl, pentyl, neopentyl, tert-pentyl, hexyl or similar groups.

In the present invention, the term "C3-C8 cycloalkyl" refers to a cyclic alkyl having 3 to 8 carbon atoms in the ring, and includes but is not limited to cyclopropyl, cyclobutyl, cyclopentyl, cyclohexyl, cycloheptyl, cyclooctyl, etc.

In the present invention, the term "aromatic ring" or "aryl" has the same meaning, preferably "C6-C10 aryl". The term "C6-C10 aryl" refers to an aromatic ring group having 6 to 10 carbon atoms in the ring that does not contain heteroatoms, such as phenyl, naphthyl, etc.

In the present invention, the term "heterocyclic aryl" or "heteroaryl" has the same meaning, refers to a heteroaryl containing one or more heteroatoms. For example, "C3-C10 heteroaryl" means an aromatic heterocycle containing 1 to 4 heteroatoms selected from the group consisting of oxygen, sulfur and nitrogen and 3-10 carbon atoms. Non-limiting examples include: furyl, thienyl, pyridyl, pyrazolyl, pyrrolyl, N-alkylpyrrolyl, pyrimidinyl, pyrazinyl, imidazolyl, tetrazolyl, etc. The heteroaryl ring may be fused to an aryl, heterocyclic or cycloalkyl ring, wherein the ring connected to the parent structure is a heteroaryl ring. Heteroaryl groups can be optionally substituted or unsubstituted.

In the present invention, the term "halogenated" means substituted by halogen.

In the present invention, the term "C2-C6 alkenyl" refers to a straight or branched chain alkenyl group having 2 to 6 carbon atoms containing a double bond, including but not limited to vinyl, propenyl, butenyl, isobutenyl, pentenyl and hexenyl, etc.

In the present invention, the term "C2-C6 alkynyl" refers to a straight-chain or branched alkynyl with 2 to 6 carbon atoms containing a triple bond, including but not limited to ethynyl, propynyl, butynyl, isobutynyl, pentynyl and hexynyl, etc.

In the present invention, the term "C1-C6 alkoxy" refers to a linear or branched alkoxy having 1 to 6 carbon atoms, including but not limited to methoxy, ethoxy, propoxy, isopropoxy, butoxy, etc. It is preferably C1-C4 alkoxy.

In the present invention, the term "substituted" means that one or more hydrogen atoms on a specific group are replaced with a specific substituent. The specific substituents are the substituents described correspondingly in the foregoing, or the substituents appearing in the respective examples. Unless otherwise specified, a substituted group may have a substituent selected from a specific group at any substitutable position of the group, and the substituent may be the same or different at each position. Those skilled in the art will understand that the combinations of substituents contemplated by the present invention are those that are stable or chemically achievable. The substituents are, for example (but not limited to): halogen, hydroxyl, carboxyl (—COOH), C1-C6 alkyl, C2-C6 alkenyl, C2-C6 alkynyl, C3-C8 cycloalkyl, 3-12 membered heterocyclic group, aryl, heteroaryl, C1-C8 aldehyde group, C2-C10 acyl, C2-C10 ester group, amino. C1-C6 alkoxy, C1-C10 sulfonyl group, etc.

In the present invention, the term "sulfonic acid group" has the following structure:

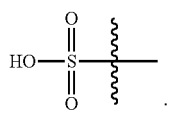

In the resent invention, the term "phosphoryl group" has the following structure:

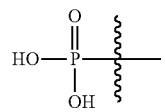

Compound

The present invention provides a compound of formula I, or its isomer, prodrug, solvate, hydrate or pharmaceutically acceptable salt thereof,

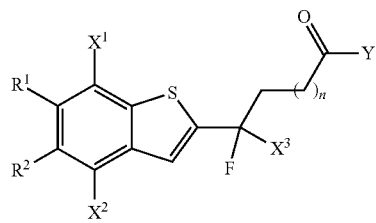

Formula I wherein $R^1$, $R^2$, $X^1$, $X^2$, $X^3$, n, and Y are as defined above.

In another preferred embodiment, in the compound, any one of $R^1$, $R^2$, $X^1$, $X^2$, $X^3$, n and Y is the corresponding group in the specific compound described in Table 1.

In another preferred embodiment, the compound is preferably a compound prepared in the examples.

In another preferred embodiment, the compound is selected from the compounds listed in Table 1.

TABLE 1

| Compound number | structure |
|---|---|
| S1 | 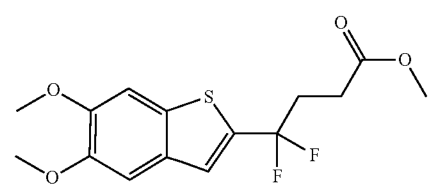 |
| S2 | 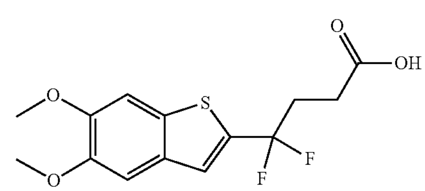 [SMILES: COc1cc2cc(C(F)(F)CCC(=O)O)sc2cc1OC] |
| S3 | 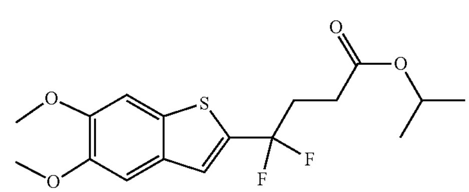 [SMILES: COc1cc2cc(C(F)(F)CCC(=O)OC(C)C)sc2cc1OC] |

TABLE 1-continued

| Compound number | structure |
| --- | --- |
| S4 | 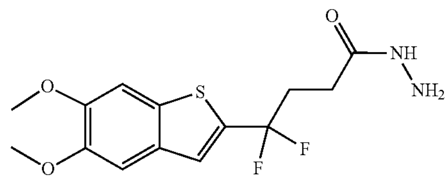 [SMILES: COc1cc2cc(C(F)(F)CCC(=O)NN)sc2cc1OC] |
| S5 | 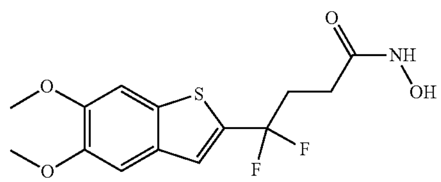 [SMILES: COc1cc2cc(C(F)(F)CCC(=O)NO)sc2cc1OC] |
| S6 | 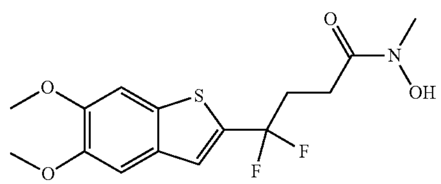 [SMILES: COc1cc2cc(C(F)(F)CCC(=O)N(C)O)sc2cc1OC] |
| S7 | 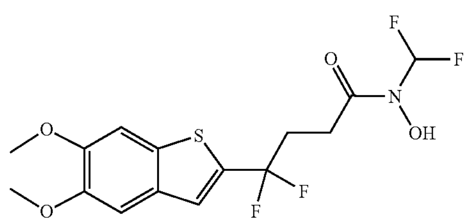 [SMILES: COc1cc2cc(C(F)(F)CCC(=O)N(O)C(F)F)sc2cc1OC] |
| S8 | 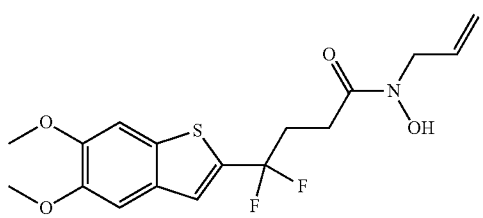 [SMILES: C=CCN(O)C(=O)CCC(F)(F)c1cc2cc(OC)c(OC)cc2s1] |
| S9 | 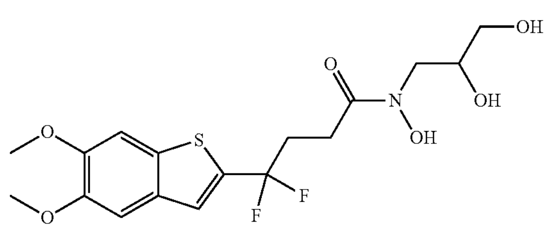 [SMILES: COc1cc2cc(C(F)(F)CCC(=O)N(O)CC(O)CO)sc2cc1OC] |
| S10 | 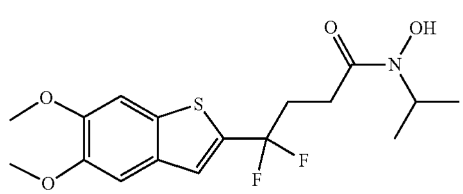 [SMILES: COc1cc2cc(C(F)(F)CCC(=O)N(O)C(C)C)sc2cc1OC] |

TABLE 1-continued
| Compound number | structure |
|---|---|
| S11 | 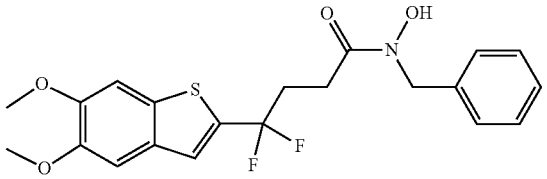 [SMILES: COc1cc2cc(C(F)(F)CCC(=O)N(O)Cc3ccccc3)sc2cc1OC] |
| S12 | 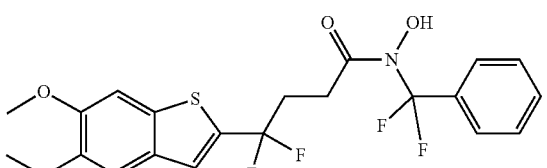 |
| S13 | 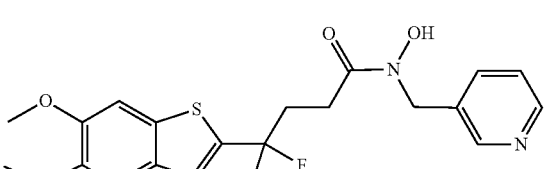 |
| S14 | 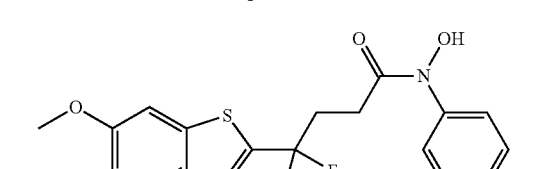 |
| S15 | 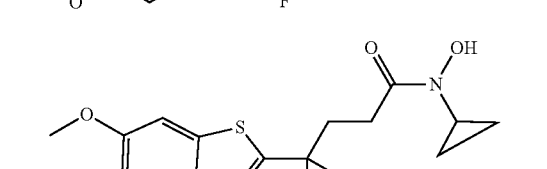 |
| S16 | 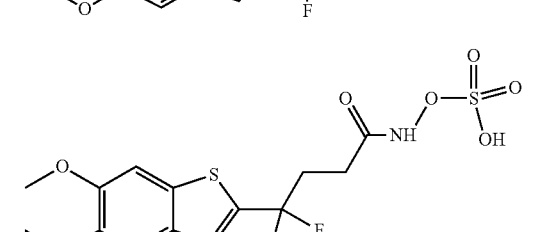 |
| S17 | 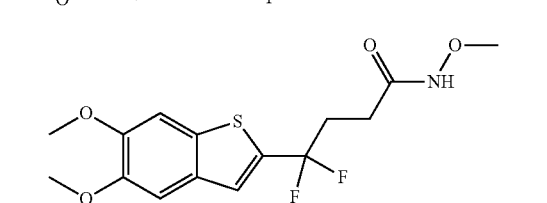 |
| S18 | 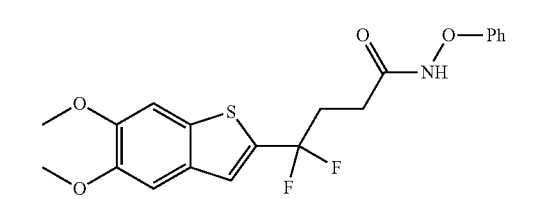 [SMILES: COc1cc2cc(C(F)(F)CCC(=O)NOc3ccccc3)sc2cc1OC] |

TABLE 1-continued

| Compound number | structure |
|---|---|
| S19 | 4-(4-fluoro-5,6-dimethoxybenzothiophen-2-yl)-4,4-difluorobutanoic acid |
| S20 | 4-(4-fluoro-5,6-dimethoxybenzothiophen-2-yl)-4,4-difluoro-N-hydroxybutanamide |
| S21 | 4-(4-fluoro-5,6-dimethoxybenzothiophen-2-yl)-4,4-difluoro-N-hydroxy-N-isopropylbutanamide |
| S22 | N-benzyl-4-(4-fluoro-5,6-dimethoxybenzothiophen-2-yl)-4,4-difluoro-N-hydroxybutanamide |
| S23 | 4-(5,6-dimethoxybenzothiophen-2-yl)-4-fluorobutanoic acid |
| S24 | 4-(5,6-dimethoxybenzothiophen-2-yl)-4-fluoro-N-hydroxy-N-isopropylbutanamide |
| S25 | 4-(5,6-dimethoxybenzothiophen-2-yl)-4-fluoro-N-hydroxy-N-phenylbutanamide |

TABLE 1-continued

| Compound number | structure |
|---|---|
| S26 | 4-(5,6-methylenedioxy-benzothiophen-2-yl)-4,4-difluorobutanoic acid |
| S27 | 4-(2,3-dihydro-[1,4]dioxino-benzothiophen-2-yl)-4,4-difluorobutanoic acid |
| S28 | 4-(5-bromo-6-methoxy-benzothiophen-2-yl)-4,4-difluorobutanoic acid |
| S29 | 4-(6-methoxy-5-vinyl-benzothiophen-2-yl)-4,4-difluorobutanoic acid |
| S30 | phenyl 4-(5,6-dimethoxy-benzothiophen-2-yl)-4,4-difluorobutanoate |
| S31 | 4-(5,6-dimethoxy-benzothiophen-2-yl)-4,4-difluorobutanoic carbonic anhydride |
| S32 | N-hydroxy-N-(carboxymethyl)-4-(5,6-dimethoxy-benzothiophen-2-yl)-4,4-difluorobutanamide |
| S33 | N-(2-hydroxyethoxy)-4-(5,6-dimethoxy-benzothiophen-2-yl)-4,4-difluorobutanamide |

Salt Type

As used herein, the term "pharmaceutically acceptable salt" refers to a salt formed by a compound of the present invention and an acid or base suitable for use as a medicine. Pharmaceutically acceptable salts include inorganic salts and organic salts. A preferred class of salts are the salts of the compounds of the invention formed with acids. Suitable acids for forming salts include, but are not limited to inorganic acids such as hydrochloric acid, hydrobromic acid, hydrofluoric acid, sulfuric acid, nitric acid, and phosphoric acid, etc.; organic acids such as formic acid, acetic acid, trifluoroacetic acid, propionic acid, oxalic acid, malonic acid, succinic acid, fumaric acid, maleic acid, lactic acid, malic acid, tartaric acid, citric acid, picric acid, benzoic acid, methylsulfonic acid, ethanesulfonic acid, p-toluenesulfonic acid, benzenesulfonic acid, and naphthalenesulfonic acid, etc.; and amino acids such as proline, phenylalanine, aspartic acid and glutamic acid, etc.

Another preferred class of salts are salts of the compounds of the invention formed with bases, such as alkali metal salt (for example sodium or potassium salt), alkaline earth metal salt (for example magnesium or calcium salt), and ammonium salt (such as lower alkanol ammonium salt and other pharmaceutically acceptable amine salt), such as methylamine salt, ethylamine salt, propylamine salt, dimethylamine salt, trimethylamine salt, diethylamine salt, triethylamine salt, tert-butylamine salt, ethylenediamine salt, hydroxyethylamine salt, dihydroxyethylamine salt, trishydroxyethylamine salt, and an amine salt formed from morpholine, piperazine, and lysine, respectively.

The term "solvate" refers to a complex in which the compound of the present invention coordinates with solvent molecules at a specific ratio. "Hydrate" refers to a complex formed by the coordination of the compound of the invention with water.

The term "prodrug" includes compounds which are themselves biologically active or inactive, when administered by an appropriate manner, which are metabolized or chemically reacted in the human body to form a compound of formula I, or salt or solution consisted of the compound of formula I. The prodrug includes, but is not limited to, a carboxylic ester, a carbonate, a phosphate, a nitrate, a sulfate, a sulfone ester, a sulfoxide ester, an amino compound, a carbamate, an azo-compound, phosphoramide, glucoside, ether, acetal, etc. of the compound.

Preparation Method

The preparation method of the compound of formula I according to the present invention is more specifically described below, but these specific methods do not constitute any limitation. The compound of the present invention may also be conveniently prepared by optionally combining various synthetic methods described in the specification or known in the art, and such combinations are readily made by those skilled in the art to which the present invention pertains.

Typically, the preparation process of the compound of the present invention is as follows, wherein the starting materials and reagents used are commercially available unless otherwise specified.

Illustratively, the preparation method of the compound is selected from the group consisting of:

Method 1:

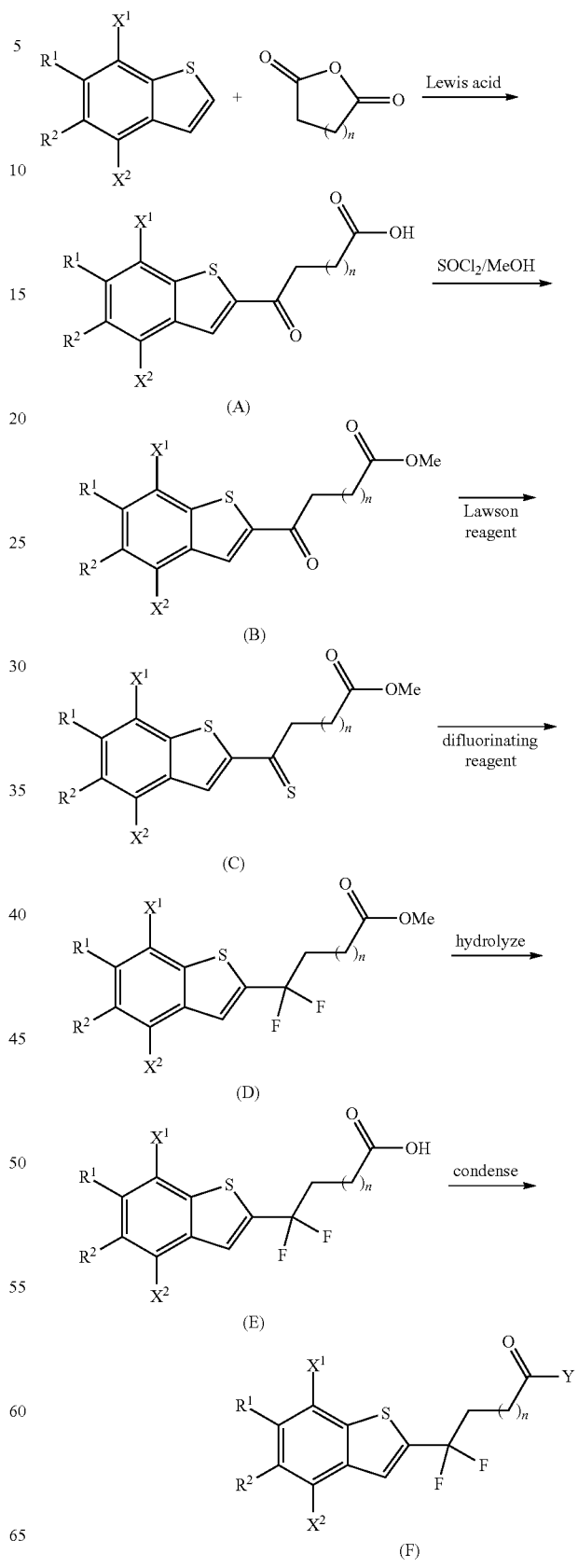

benzothiophene is reacted with cyclic anhydride to obtain acid A, then undergoes methyl esterification to obtain B, then carbonyl is vulcanized to obtain C, further reacted under the condition of difluorinating reagent to obtain D, methyl ester is hydrolyzed to obtain E, and finally condensed with HY to obtain F; wherein $R_1$, $R_2$, $X_1$, $X_2$, n, and Y are as defined above;

Method 2:

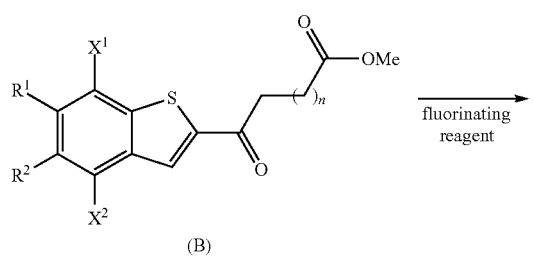

(B)

-continued

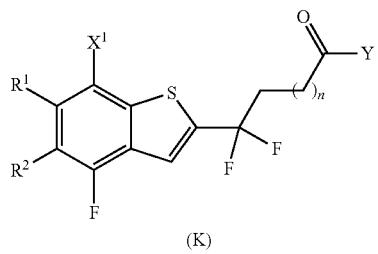

(K)

B is reacted with SELECTFLUOR™, a selective fluorine reagent (1-chloromethyl-4-fluoro-1,4-diazobicyclo 2.2.2 octane bis(tetrafluoroborate) salt), to obtain G, then reacted with Lawson reagent to obtain H, then further reacted with DAST to obtain I, hydrolyzed to obtain J, and finally condensed with HY to obtain K; wherein $X^2$=H, $R^1$, $R^2$, $X^1$, n, Y are as defined above;

Method 3:

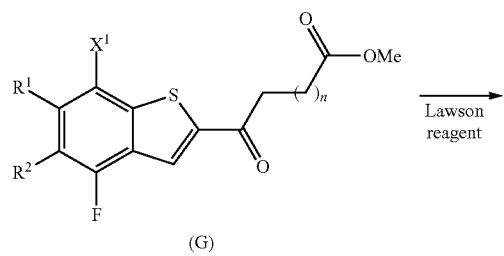

(G)

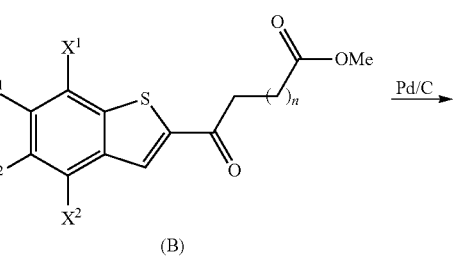

(B)

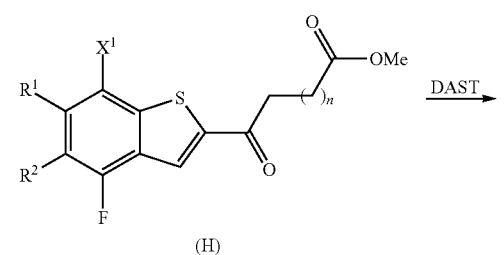

(H)

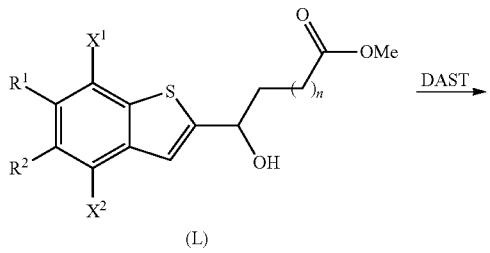

(L)

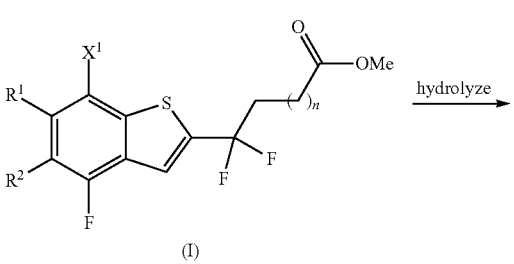

(I)

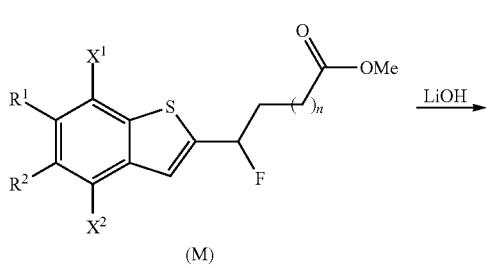

(M)

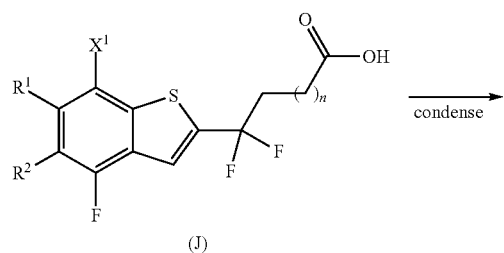

(J)

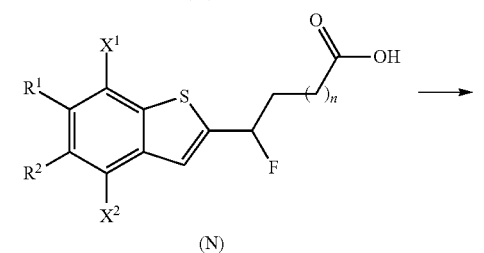

(N)

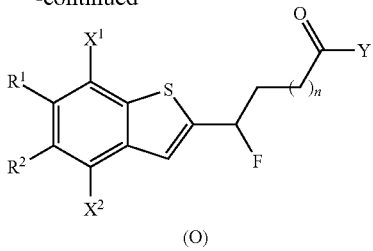

(O)

B is hydrogenated under Pd/C conditions to obtain L, then reacted with DAST to obtain M, further hydrolyzed to obtain N, and finally condensed with HY to obtain O; wherein $R^1$, $R^2$, $X^1$, $X^2$, n and Y are as defined above.

Pharmaceutical Composition and Method for Administration

The present invention also provides a pharmaceutical composition comprising:

(i) one or more therapeutically effective amount of the compound, or its isomer, prodrug, solvate, hydrate or pharmaceutically acceptable salt thereof; and (ii) a pharmaceutically acceptable carrier.

Because the compound of the present invention has excellent anti-tumor activity, the compound of the present invention and its various crystal forms, pharmaceutically acceptable inorganic or organic salts, hydrates or solvates, and pharmaceutical compositions containing the compound of the present invention as the main active ingredient can be used to treat, prevent, and alleviate tumor-related diseases.

The pharmaceutical composition of the present invention comprises a safe and effective amount of a compound of the present invention or a pharmacologically acceptable salt thereof, and a pharmacologically acceptable excipient or carrier. In which, "safe and effective amount" is meant that the amount of the compound is sufficient to significantly improve the condition without causing serious side effects. The therapeutically effective amount is determined according to the age, condition, and course of treatment of the subject. Generally, the pharmaceutical composition contains 1-2000 mg of the compound of the present invention/dose, more preferably, 10-1000 mg of the compound of the present invention/dose. Preferably, the "a dose" is a capsule or tablet.

The "pharmaceutically acceptable carrier" refers to: one or more compatible solids or liquid fillers or gel materials, which are suitable for human use, and must have sufficient purity and low toxicity. "Compatibility" means that each component in the composition can be admixed with the compounds of the present invention and with each other without significantly reducing the efficacy of the compounds. Some examples of pharmaceutically acceptable carrier include sugar (such as glucose, sucrose, lactose, etc.), starch (such as corn starch, potato starch, etc.), cellulose and derivatives (such as sodium carboxymethyl cellulose, sodium ethyl cellulose, cellulose acetate, etc.), gelatin, talc, solid lubricants (such as stearic acid, magnesium stearate), calcium sulfate, vegetable oils (such as soybean oil, sesame oil, peanut oil, olive oil, etc.), polyols (such as propylene glycol, glycerol, mannitol, sorbitol, etc.), emulsifiers (such as Tween), wetting agent (such as sodium dodecyl sulfate), coloring agents, flavoring agents, stabilizers, antioxidants, preservatives, pyrogen-free water, etc.

The administration mode of the compound or pharmaceutical composition of the present invention is not particularly limited, and representative administration modes include, but are not limited to oral, intratumoral, rectal, parenteral (intravenous, intramuscular or subcutaneous) and topical administration.

Solid dosage forms for oral administration include capsules, tablets, pills, powders and granules. In these solid dosage forms, the active ingredient is mixed with at least one conventional inert excipient (or carrier), such as sodium citrate or dicalcium phosphate, or mixed with any of the following components: (a) fillers or compatibilizer, such as starch, lactose, sucrose, glucose, mannitol and silicic acid; (b) binders, such as hydroxymethyl cellulose, alginate, gelatin, polyvinylpyrrolidone, sucrose and arabic gum; (c) humectants, such as, glycerol; (d) disintegrating agents such as agar, calcium carbonate, potato starch or tapioca starch, alginic acid, certain composite silicates, and sodium carbonate; (e) dissolution-retarding agents, such as paraffin; (f) absorption accelerators, such as quaternary ammonium compounds; (g) wetting agents, such as cetyl alcohol and glyceryl monostearate; (h) adsorbents, such as kaolin; and (i) lubricants such as talc, calcium stearate, magnesium stearate, solid polyethylene glycol, sodium lauryl sulfate, or the mixture thereof. In capsules, tablets and pills, the dosage forms may also contain buffering agents.

Solid dosage forms such as tablets, dragees, capsules, pills and granules can be prepared with coatings and shells such as enteric coatings and other materials known in the art. They may contain opacifying agents and the release of the active compound or compound in such compositions may be released in a portion of the digestive tract in a delayed manner. Examples of embedding components that can be employed are polymeric materials and waxy materials. If necessary, the active compound may also be in microencapsulated form with one or more of the above-mentioned excipients.

Liquid dosage forms for oral administration include pharmaceutically acceptable emulsions, solutions, suspensions, syrups or tinctures. In addition to the active compound, the liquid dosage form may contain inert diluents conventionally used in the art, such as water or other solvents, solubilizers and emulsifiers, such as ethanol, isopropanol, ethyl carbonate, ethyl acetate, propylene glycol, 1,3-butanediol, dimethylformamide and oils, especially cottonseed oil, peanut oil, corn germ oil, olive oil, castor oil and sesame oil or mixtures of these substances.

In addition to these inert diluents, the compositions may contain adjuvants such as wetting agents, emulsifying and suspending agents, sweetening agents, flavoring agents and spices.

In addition to the active compound, the suspension may contain suspending agent, such as ethoxylated isooctadecanol, polyoxyethylene sorbitol and dehydrated sorbitan ester, microcrystalline cellulose, aluminum methoxide and agar, or the mixture thereof etc.

The compositions for parenteral injection may comprise physiologically acceptable sterile aqueous or anhydrous solutions, dispersions, suspensions or emulsions, and sterile powders which can be re-dissolved into sterile injectable solutions or dispersions. Suitable aqueous and non-aqueous carriers, diluents, solvents or excipients include water, ethanol, polyols and any suitable mixtures thereof.

Dosage forms for the compounds of the invention for topical administration include ointments, powders, patches, sprays and inhalants. The active ingredient is mixed under sterile conditions with a physiologically acceptable carrier and any preservatives, buffers, or propellants which may be required if necessary.

The benzothiophene derivative represented by the above general formula I and its pharmaceutically acceptable salt in the present invention can be administered alone or in combination with other pharmaceutically acceptable therapeutic agents, especially in combination with traditional cytotoxic chemotherapy drugs and tumor immune checkpoint inhibitors. The pharmaceutically acceptable therapeutic agent includes, but is not limited to, other acceptable therapeutic agents that are used in combination with the benzothiophene derivative represented by the general formula I, such as the immune checkpoint inhibitor monoclonal antibody drugs OPDIVO® (nivolumab) and KEYTRUDA® (pembrolizumab), directly acting on the PD-1 protein on the surface of T cells, interrupting the interaction of PD-1/PD-L1; and traditional cytotoxic chemotherapy small molecule drugs, such as the anti-tumor drugs that affect nucleic acid synthesis methotrexate (MTX), 5-fluorouracil (5FU), etc., anti-tumor drugs that affect nucleic acid transcription, such as adriamycin, epirubicin, aclarithromycin, and mithramycin, and anti-tumor drugs that act on tubulin synthesis, such as paclitaxel and vinorelbine etc., aromatase inhibitors such as aminoglutethimide, cell signaling pathway inhibitors such as epidermal growth factor receptor inhibitors imatinib, gefitinib, erlotinib, lapatinib, etc. The components of the combination can be administered simultaneously or sequentially, in the form of a single formulation or in the form of different formulations. The combination includes not only the combination of the compound of the present invention and one other active agent, but also the combination of the compound of the present invention and two or more other active agents.

The treatment method of the present invention can be administered alone or in combination with other treatment means or therapeutic drugs.

When the pharmaceutical composition is used, a safe and effective amount of the compound of the present invention is applied to a mammal in need of treatment (such as a human), wherein the dosage at the time of administration is the pharmaceutically effective dosage, for people having a body weight of 60 kg, the daily dose is usually 1~2000 mg, preferably 50~1000 mg. Of course, specific doses should also consider factors such as the administration route, the health of the patient, etc., which are within the skill of the skilled physician.

Compared with the prior art, the present invention has the following main advantages:
(1) The compound has the characteristics of simple structure, easy synthesis, stable metabolism, high safety, and various administration modes;
(2) The compound has excellent activation performance for interferon gene stimulating protein, thus activating T cells and significantly promoting the expression of interferon factor IFN-β, thereby realizing effective treatment of tumors and their complications;
(3) Compared with the compound 1a disclosed in TW201817723A (US20180093964), the compound has significantly improved agonistic activity on interferon gene stimulating proteins, with about 2-2.5-fold enhancement. In addition, the compound S2 of the present patent is also significantly superior to the compound 1a disclosed in TW201817723A (US20180093964) in terms of pharmacokinetic properties, especially the plasma exposure during intravenous injection which is about 4.4 times of that of 1a.

The present invention will be further described below in conjunction with specific examples, but these examples do not limit the scope of the present invention.

For the following examples, standard operations and purification methods known to those skilled in the art can be used. Unless otherwise specified, raw materials are usually available from commercially available sources, such as Aldrich Chemicals Co. and Acros Organics. Commercially available solvents and reagents are generally used without further purification, anhydrous solvents are all processed by standard methods, and other reagents are commercially available analytically pure. Unless otherwise specified, all temperatures are expressed in ° C. (degrees Celsius), and room temperature or ambient temperature refers to 20-25° C. The structure of the compound is determined by the nuclear magnetic resonance spectrum (NMR). The nuclear magnetic resonance spectrum displacement (δ) is given in units of one million (ppm). The nuclear magnetic resonance spectrum is measured with a Mercury-300 MHz nuclear magnetic resonance instrument, with deuterated chloroform ($CDCl_3$) and deuterated methanol ($CD_3OD$) as solvents and tetramethylsilane (TMS) as internal standard.

The chromatography column generally uses 200-300 mesh silica gel as the carrier.

In the above discussion and the following examples, the following abbreviations have the following meanings. If an abbreviation is not defined, it has the generally accepted meaning.

RT is room temperature;
DIPEA is N,N-diisopropylethylamine;
THF is tetrahydrofuran:
TBTU is O-benzotriazole-N, N, N', N'-tetramethylurea tetrafluoroboric acid;
SELECTFLUOR™ is 1-chloromethyl-4-fluoro-1,4-diazobicyclo 2.2.2 octane bis(tetrafluoroborate) salt;
DAST is diethylaminosulfur trifluoride.

I. Compound Preparation Examples

The following preparation examples exemplarily prepare part of the compounds of formula I of the present invention, and each compound is represented by S1 to S33.
1. Synthesis of Compound S1

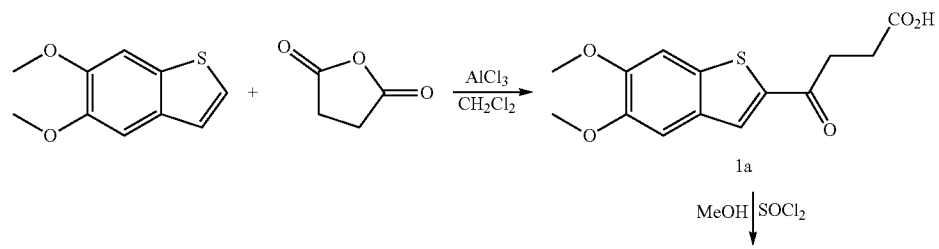

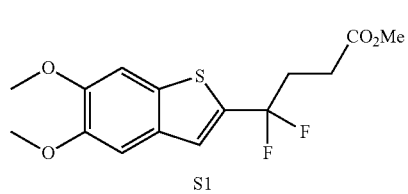 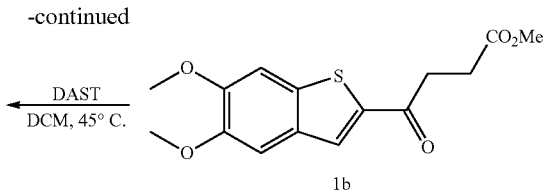

Step 1: succinic anhydride (1.55 g, 1.44 mmol) and aluminum trichloride (2.75 g, 20.6 mmol) were weighed out and dissolved in 10 mL 1,2-dichloroethane, and stirred at −10° C.; 5,6-dimethoxybenzo[b]thiophene (2.0 g, 10.30 mmol) was dissolved in 40 mL 1,2-dichloroethane and then dropped into the above reaction solution dropwise for 30 minutes; after the dropping, continued stirring for 10 minutes, then transferred to 45° C. oil bath for reaction overnight. TLC was used to monitor the completion of the reaction, then the reaction solution was poured into ice water, 60 mL of 15% hydrochloric acid solution was added, stirred to precipitate the product, and filtered with suction to obtain the crude product. The pure product 1a (2.35 g, yield 77.6%) was obtained after recrystallization from dichloromethane. $^1$H NMR (400 MHz, DMSO) δ 12.18 (s, 1H), 8.19 (s, 1H), 7.58 (s, 1H), 7.46 (s, 1H), 3.85 (s, 3H), 3.82 (s, 3H), 3.25 (t, t, J=6.4 Hz, 2H), 2.58 (t, J=6.4 Hz, 2H).

Step 2: The compound 1a (1 eq) was dissolved in methanol, and chlorinated sulfoxide (5 eq) was added dropwise at 0° C., and then moved to room temperature to react for 4 hours. After the reaction was completed, the solvent was spin-dried, and a small amount of water was added and the pH was adjusted to about 8 with saturated sodium bicarbonate solution, extracted with ethyl acetate, and the organic phase was collected and purified by column to obtain compound 1b;

Step 3: compound 1b (1 eq) was dissolved in dichloromethane, and DAST (5 eq) was added under an ice bath, after about 10 minutes, the temperature was warmed to 45° C., reacted for two hours, after the reaction solution was cooled to room temperature, quenched with saturated sodium bicarbonate solution under ice bath, extracted with ethyl acetate, separated and purified by column to obtain compound S1. $^1$H NMR (400 MHz, CDCl$_3$) δ7.34 (s, 1H), 7.25 (s, 1H), 7.20 (s, 1H), 3.95 (s, 3H), 3.94 (s, 3H), 3.67 (s, 3H), 2.72-2.61 (m, 2H), 2.61-2.55 (m, 2H); MS (EI): 330.0.

2. Synthesis of Compound S2

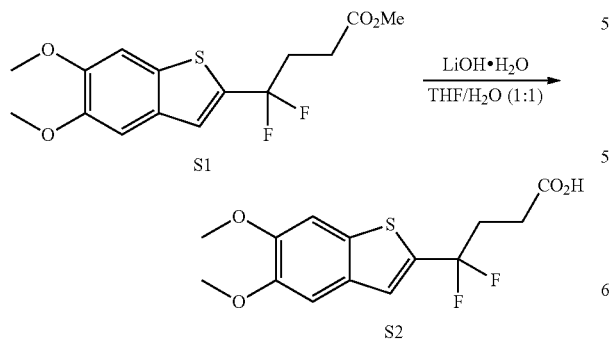

Compound S1 (1 eq) was dissolved in a mixed solvent of tetrahydrofuran:water (1:1), and then lithium hydroxide monohydrate (3 eq) was added, reacted for half an hour at room temperature, and the pH was adjusted to be 5-6 with 1N hydrochloric acid, extracted with chloroform, and collected the organic phase, purified by column to obtain compound S2. $^1$H NMR (400 MHz, CDCl$_3$) δ 7.35 (s, 1H), 7.25 (s, 1H), 7.20 (s, 1H), 3.96 (s, 3H), 3.94 (s, 3H), 2.70-2.58 (m, 4H); MS (EI): 316.

3. Synthesis of Compound S3

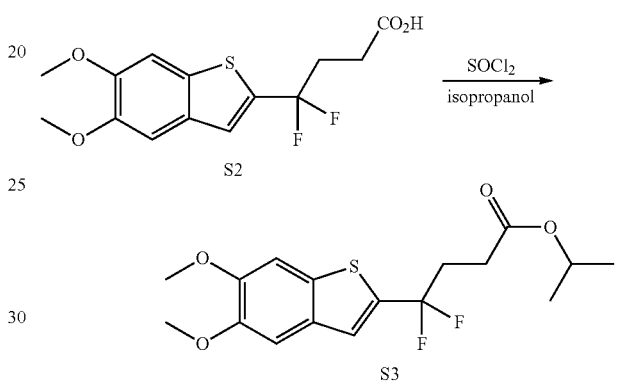

Compound S2 (1 eq) was dissolved in isopropanol, and then chlorinated sulfoxide (5 eq) was added dropwise at 0° C., and then moved to room temperature to react for 4 hours. After the reaction was completed, the solvent was spin-dried, and a small amount of water was added and the pH was adjusted to about 8 with saturated sodium bicarbonate solution, extracted with ethyl acetate, and the organic phase was collected and purified by column to obtain compound S3. $^1$H NMR (400 MHz, CDCl$_3$) δ 7.85 (s, 1H), 7.22 (s, 1H), 7.19 (s, 1H), 3.97 (s, 3H), 3.94 (s, 3H), 3.68 (m, 1H), 3.31 (t, 2H, J=6.8 Hz), 2.78 (t, 2H. J=6.8 Hz), 1.13 (d, 6H, J=4.0 Hz); MS (EI): 358.

4. Synthesis of Compound S4

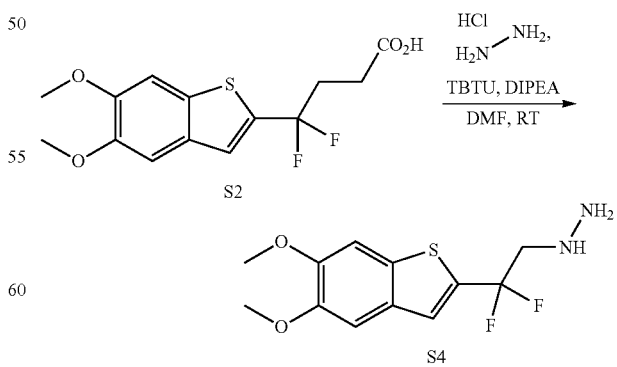

Compound S2 (1 eq) was dissolved in N, N-dimethylformamide, and then hydrazine hydrochloride (1.0 eq), TBTU (3 eq), and N, N-diisopropylethylamine (5 eq) were added sequentially, and reacted overnight at room temperature. After the reaction was completed, the reaction solution was poured into ice water, extracted with ethyl acetate, and the organic phase was collected and purified by column to obtain compound S4. H NMR (400 MHz, DMSO-d6) δ9.82 (s, 1H), 8.10 (s, 1H), 7.53 (s, 1H), 7.44 (s, 1H), 3.89 (s, 3H), 3.86 (s, 3H), 2.62-2.53 (m, 4H); MS (EI): 330.

5. Synthesis of Compound S5

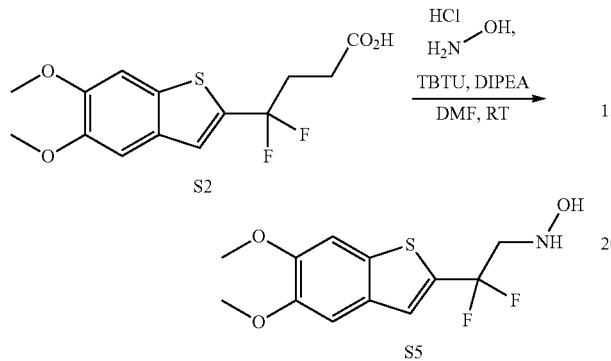

Compound S2 (1 eq) was dissolved in N, N-dimethylformamide, and then hydroxylamine hydrochloride (1.0 eq), condensing agent TBTU (3 eq), and N,N-diisopropylethylamine (5 eq) were added sequentially, and reacted overnight at room temperature. After the reaction was completed, the reaction solution was poured into ice water, extracted with ethyl acetate, and the organic phase was collected and purified by column to obtain compound S5. $^1$H NMR (400 MHz, CDCl$_3$+CD$_3$OD) δ 7.39 (s, 1H), 7.26 (s, 1H), 7.21 (s, 1H), 3.95 (s, 3H), 3.93 (s, 3H), 2.59-2.50 (m, 4H); MS (EI): 331.

6. Synthesis of Compound S6

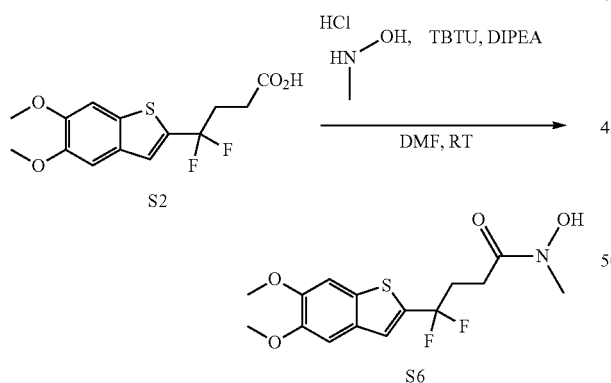

Compound S2 (1 eq) was dissolved in N, N-dimethylformamide, and then N-methylhydroxylamine hydrochloride (1.5 eq), TBTU (3 eq), and N,N-diisopropylethylamine (5 eq) were added sequentially, and reacted overnight at room temperature. After the reaction was completed, the reaction solution was poured into ice water, extracted with ethyl acetate, and the organic phase was collected and purified by column to obtain compound S6. $^1$H NMR (400 MHz, DMSO) δ 7.79 (s, 1H), 7.26 (s, 1H), 7.24 (s, 1H), 3.97 (s, 3H), 3.95 (s, 3H), 3.28 (s, 3H), 2.67-2.53 (m, 4H); MS (EI): 345.

7. Synthesis of Compound S7

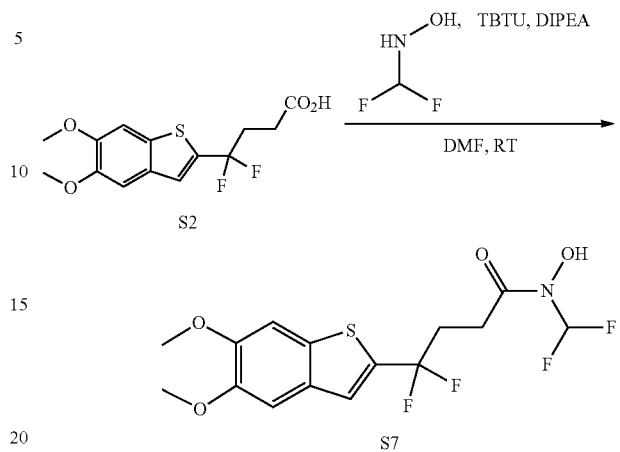

Compound S2 (1 eq) was dissolved in N, N-dimethylformamide, and then N-difluoromethyl hydroxylamine (1.0 eq), condensing agent TBTU (3 eq), and N,N-diisopropyl ethylamine (5 eq) were added sequentially, and reacted overnight at room temperature. After the reaction was completed, the reaction solution was poured into ice water, extracted with ethyl acetate, and the organic phase was collected and purified by column to obtain compound S7. $^1$H NMR (400 MHz, CDCl$_3$) δ 7.94 (s, 1H), 7.25 (s, 1H), 7.24 (s, 1H), 7.20 (m, 1H), 3.95 (s, 3H), 3.93 (s, 3H), 3.38 (t, 2H. J=8.0 Hz), 2.97 (t, 2H, J=8.0 Hz): MS (EI): 381.

8. Synthesis of Compound S8

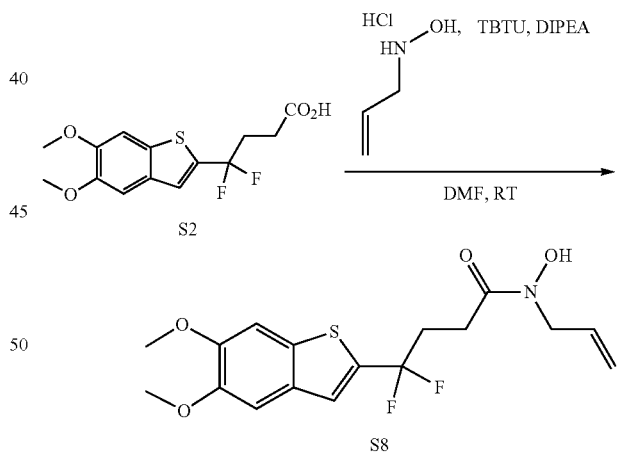

Compound S2 (0 eq) was dissolved in N, N-dimethylformamide, and N-allylhydroxylamine hydrochloride (1.5 eq), TBTU (3 eq), and N,N-diisopropylethyl amine (5 eq) were added sequentially, and reacted overnight at room temperature. After the reaction was completed, the reaction solution was poured into ice water, extracted with ethyl acetate, and the organic phase was collected and purified by column to obtain compound S8. $^1$H NMR (400 MHz, CDCl$_3$) δ8.10 (brs, 1H), 7.72 (s, 1H), 7.35 (s, 1H), 7.13 (s, 1H), 5.61 (m, 1H), 5.33 (m, 2H), 3.96 (s, 3H), 3.92 (s, 3H), 3.70 (d, 2H, J=6.2 Hz), 2.65-2.54 (m, 4H); MS (EI): 371.

9. Synthesis of Compound S9

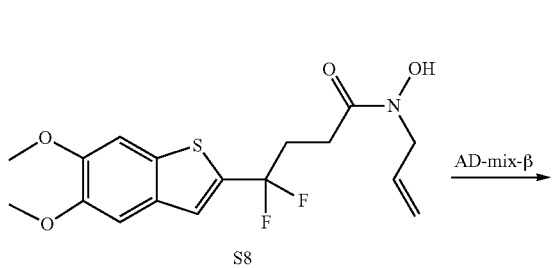

Compound S8 (1 eq) was dissolved in 1,4-dioxane, followed by adding dihydroxy-mixture reagent AD-Mix-β (1.5 eq) to react overnight at room temperature. After the reaction was completed, the reaction solution was poured into ice water, extracted with dichloromethane, and the organic phase was collected and purified by column to obtain compound S9. $^1$H NMR (400 MHz, CD$_3$OD) δ 8.30 (brs, 1H), 7.99 (s, 1H), 7.37 (s, 1H), 7.22 (s, 1H), 4.01 (m, 1H), 3.96 (s, 3H), 3.94 (s, 3H), 3.84 (m, 2H), 3.65 (m, 2H), 2.62-2.55 (m, 4H); MS (EI): 405.

10. Synthesis of Compound S10

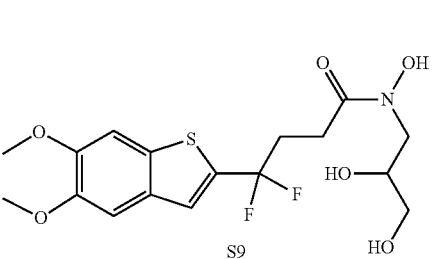

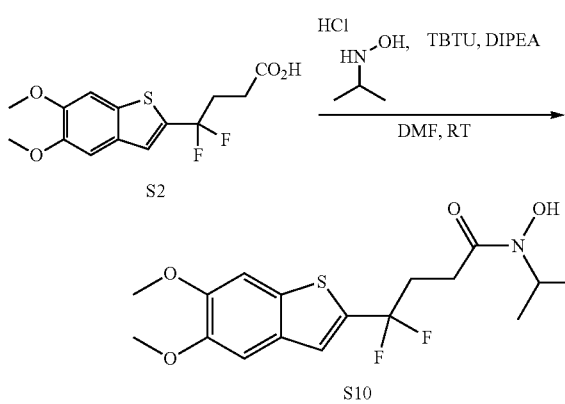

Compound S2 (1 eq) was dissolved in N, N-dimethylformamide, and then N-isopropylhydroxylamine hydrochloride (1.5 eq), TBTU (3 eq), and N,N-diisopropylethyl amine (5 eq) were added sequentially, and reacted overnight at room temperature. After the reaction was completed, the reaction solution was poured into ice water, extracted with ethyl acetate, and the organic phase was collected and purified by column to obtain compound S10. $^1$H NMR (400 MHz, CDCl$_3$) δ 7.85 (s, 1H), 7.28 (brs, 1H), 7.23 (s, 1H), 7.20 (s, 1H), 3.99 (s, 3H), 3.97 (s, 3H), 3.23 (m, 1H), 2.65-2.60 (m, 4H), 1.10 (d, 6H, J=4.0 Hz); MS (EI): 373.

11. Synthesis of Compound S11

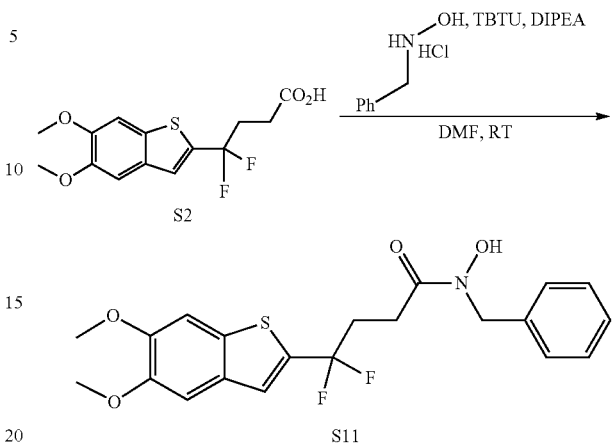

Compound S2 (1 eq) was dissolved in N, N-dimethylformamide, and then N-benzylhydroxylamine hydrochloride (1.5 eq), TBTU (3 eq), and N,N-diisopropylethylamine (5 eq) were added sequentially, and reacted overnight at room temperature. After the reaction was completed, the reaction solution was poured into ice water, extracted with ethyl acetate, and the organic phase was collected and purified by column to obtain compound S11. $^1$H NMR (400 MHz, CDCl$_3$) δ 7.82 (s, 1H), 7.73 (brs, 1H), 7.37-7.3 (m, 5H), 7.23 (s, 1H), 7.20 (s, 1H), 4.14 (s, 2H), 3.99 (s, 3H), 3.97 (s, 3H), 2.59-2.53 (m, 4H), MS (EI): 421.

12. Synthesis of Compound S12

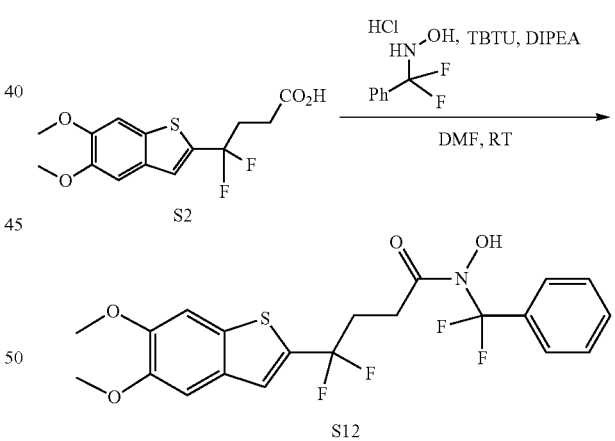

Compound S2 (1 eq) was dissolved in N, N-dimethylformamide, and then N-difluorobenzylhydroxylamine hydrochloride (1.5 eq). TBTU (3 eq), and N,N-diisopropyl ethylamine (5 eq) were added sequentially, and reacted overnight at room temperature. After the reaction was completed, the reaction solution was poured into ice water, extracted with ethyl acetate, and the organic phase was collected and purified by column to obtain compound S12. $^1$H NMR (400 MHz, CDCl$_3$) δ 7.90 (s, 1H), 7.76 (brs, 1H), 7.59-7.52 (m, 5H), 7.38 (s, 1H), 7.29 (s, 1H), 3.95 (s, 3H), 3.93 (s, 3H), 2.68-2.62 (m, 4H), MS (EI): 457.

13. Synthesis of Compound S13

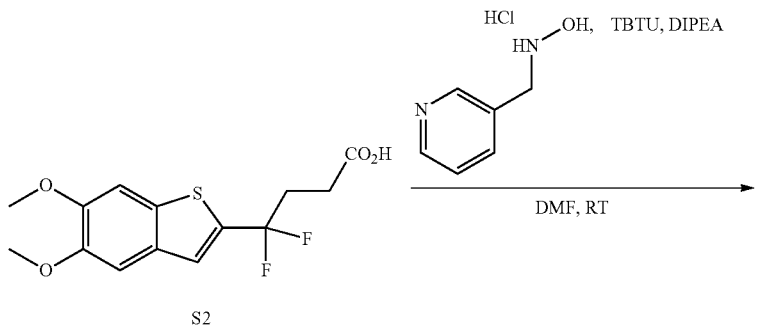

Compound S2 (1 eq) was dissolved in N, N-dimethylformamide, and then N-pyridinemethylene hydroxylamine hydrochloride (1.5 eq), TBTU (3 eq), and N,N-diisopropyl ethylamine (5 eq) were added sequentially, and reacted overnight at room temperature. After the reaction was completed, the reaction solution was poured into ice water, extracted with ethyl acetate, and the organic phase was collected and purified by column to obtain compound S13. $^1$H NMR (400 MHz, CDCl$_3$) δ 8.45 (s, 1H), 8.17 (d, 1H, J=7.5 Hz), 7.82 (s, 1H), 7.79 (d, 1H, J=7.5 Hz), 7.70 (brs, 1H), 7.28 (m, 1H), 7.25 (s, 1H), 7.20 (s, 1H), 4.21 (s, 2H), 3.97 (s, 3H), 3.95 (s, 3H), 2.66-2.59 (m, 4H), MS (EI): 422.

14. Synthesis of Compound S14

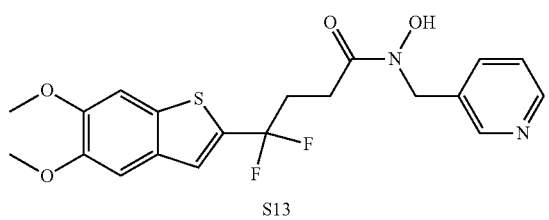

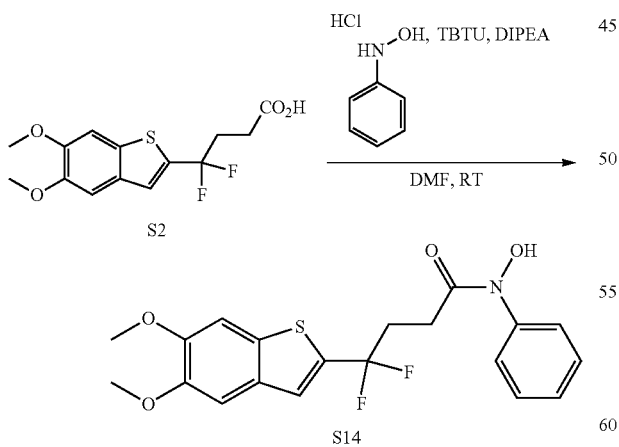

Compound S2 (1 eq) was dissolved in N, N-dimethylformamide, and then N-phenylhydroxylamine hydrochloride (1.5 eq), TBTU (3 eq), and N,N-diisopropylethylamine (5 eq) were added sequentially, and reacted overnight at room temperature. After the reaction was completed, the reaction solution was poured into ice water, extracted with ethyl acetate, and the organic phase was collected and purified by column to obtain compound S14. $^1$H NMR (400 MHz, CDCl$_3$) δ 8.00 (s, 1H), 7.79 (brs, 1H), 7.50-7.42 (m, 5H), 7.29 (s, 1H), 7.22 (s, 1H), 3.99 (s, 3H), 3.97 (s, 3H), 2.62-2.54 (m, 4H); MS (EI): 407.

15. Synthesis of Compound S15

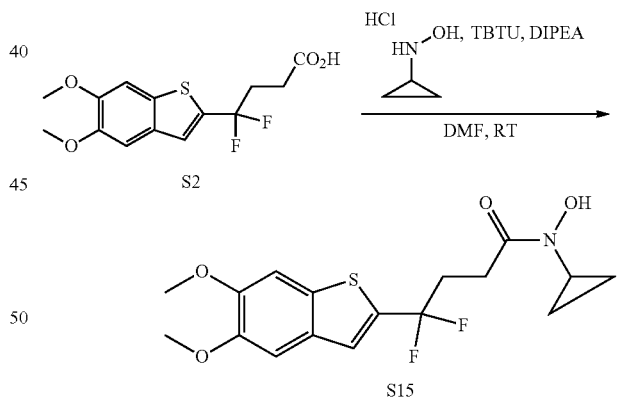

Compound S2 (1 eq) was dissolved in N, N-dimethylformamide, and then N-cyclopropylhydroxylamine hydrochloride (1.0 eq), condensing agent TBTU (3 eq), and N,N-diisopropylethylamine (5 eq) were added sequentially, and reacted overnight at room temperature. After the reaction was completed, the reaction solution was poured into ice water, extracted with ethyl acetate, and the organic phase was collected and purified by column to obtain compound S15. $^1$H NMR (400 MHz, CDCl$_3$) δ 7.94 (s, 1H), 7.28 (s, 1H), 7.24 (s, 1H), 3.96 (s, 3H), 3.95 (s, 3H), 3.28 (m, 1H), 2.61-2.52 (m, 4H), 0.94 (m, 4H); MS (EI): 371.

16. Synthesis of Compound S16

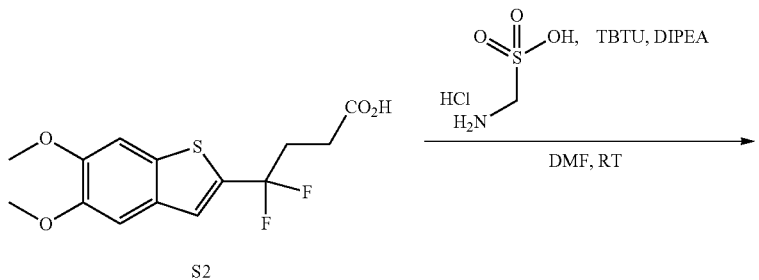

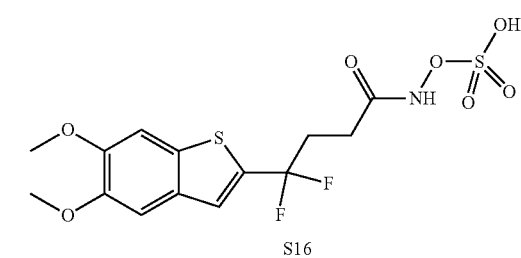

Compound S2 (1 eq) was dissolved in N, N-dimethylformamide, and then hydroxylamine sulfonate hydrochloride (1.0 eq), condensing agent TBTU (3 eq), and N,N-diisopropylethylamine (5 eq) were added sequentially, and reacted overnight at room temperature. After the reaction was completed, the reaction solution was poured into ice water, extracted with ethyl acetate, and the organic phase was collected and purified by column to obtain compound S16. $^1$H NMR (400 MHz, CDCl$_3$+CD$_3$OD) δ 11.89 (brs, 1H,), 7.40 (s, 1H), 7.24 (s, 1H), 7.19 (s, 1H), 3.97 (s, 3H), 3.96 (s, 3H), 2.67-2.58 (m, 4H); MS (EI): 411.

17. Synthesis of Compound S17

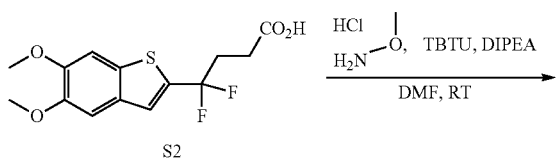

-continued

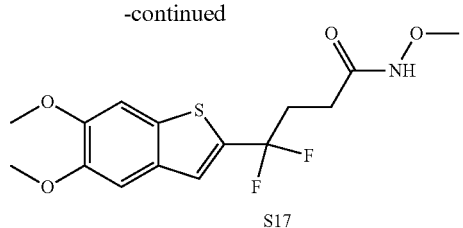

Compound S2 (1 eq) was dissolved in N, N-dimethylformamide, and then methoxyamine hydrochloride (1.5 eq), TBTU (3 eq), and N,N-diisopropylethylamine (5 eq) were added sequentially, and reacted overnight at room temperature. After the reaction was completed, the reaction solution was poured into ice water, extracted with ethyl acetate, and the organic phase was collected and purified by column to obtain compound S17. $^1$H NMR (400 MHz, CDCl$_3$) δ 8.54 (brs 1H), 7.87 (s, 1H), 7.20 (s, 2H), 3.97 (s, 3H), 3.96 (s, 3H), 3.79 (s, 3H), 2.69-2.60 (m, 4H); MS (EI): 345.

18. Synthesis of Compound S18

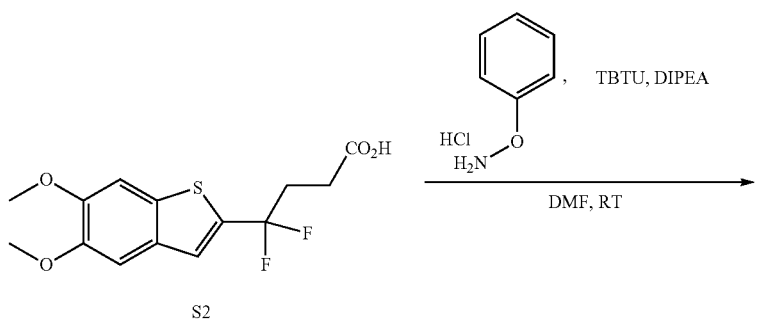

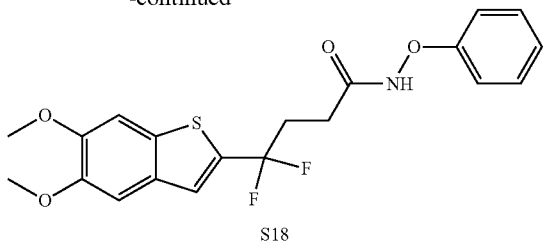

S18

Compound S2 (1 eq) was dissolved in N, N-dimethylformamide, and then O-phenylhydroxylamine hydrochloride (1.5 eq), TBTU (3 eq), and N,N-diisopropylethylamine (5 eq) were added sequentially, and reacted overnight at room temperature. After the reaction was completed, the reaction solution was poured into ice water, extracted with ethyl acetate, and the organic phase was collected and purified by column to obtain compound S18. $^1$H NMR (400 MHz, CDCl$_3$) δ 8.33 (s, 1H), 7.65 (s, 1H), 7.24-6.95 (m, 6H), 3.96 (s, 3H), 3.95 (s, 3H), 2.67-2.59 (m, 4H); MS (EI): 407.

19. Synthesis of Compound S19 bonate solution under ice bath, extracted with ethyl acetate, separated and purified by column to obtain difluoride intermediate. The difluorine intermediate was dissolved in 1,4-dioxane, followed by an appropriate amount of 6N hydrochloric acid, refluxed overnight. After the reaction was completed, the reaction solution was cooled to room temperature, the solvent was spin-dried and recrystallized with ethanol to obtain compound S19. $^1$H NMR (400 MHz, CDCl$_3$) δ 12.09 (s, 1H), 8.12 (s, 1H), 7.48 (s, 1H), 3.94 (s, 3H), 3.89 (s, 3H), 2.90-2.58 (m, 4H); MS(EI): 334.

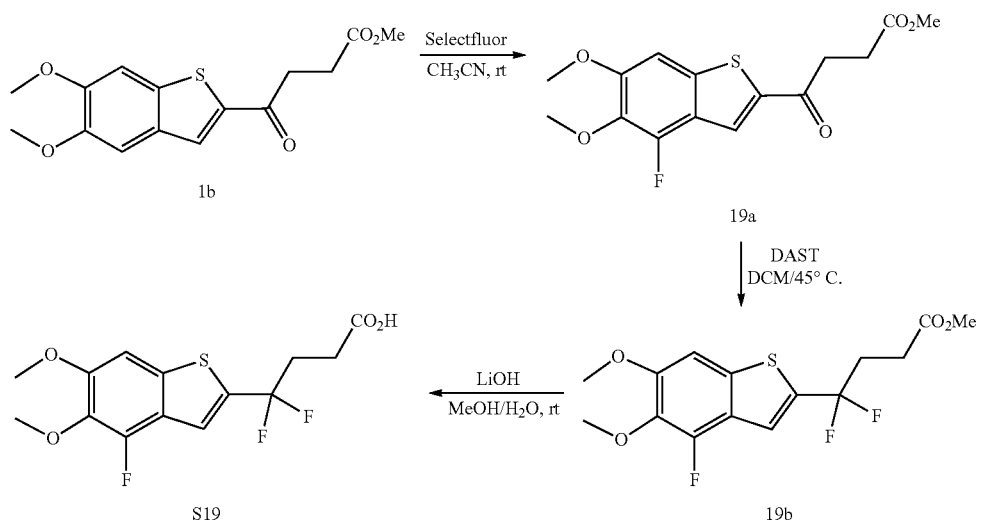

Step 1: compound 1b (1 eq) was dissolved in acetonitrile, and the selective fluoride reagent SELECTFLUOR™ was added at room temperature, and reacted overnight. After the reaction was completed, quenched with saturated sodium bicarbonate solution, extracted with ethyl acetate, and then the organic phase was collected and purified by column to obtain compound 19a;

Step 2: compound 19a (1 eq) was dissolved in dichloromethane, and DAST (5 eq) was added under ice bath, after about 10 minutes, the temperature was warmed to 45° C., and reacted for two hours, after the reaction solution was cooled to room temperature, quenched with saturated sodium bicarbonate solution under ice bath, extracted with ethyl acetate, separated and purified by column to obtain compound 19b;

Step 3: compound 19b (1 eq) was dissolved in dichloromethane, and DAST (5 eq) was added under ice bath, after about 10 minutes, the temperature was warmed to 45° C., reacted for two hours, after the reaction solution was cooled to room temperature, quenched with saturated sodium bicar- 20. Synthesis of Compound S20

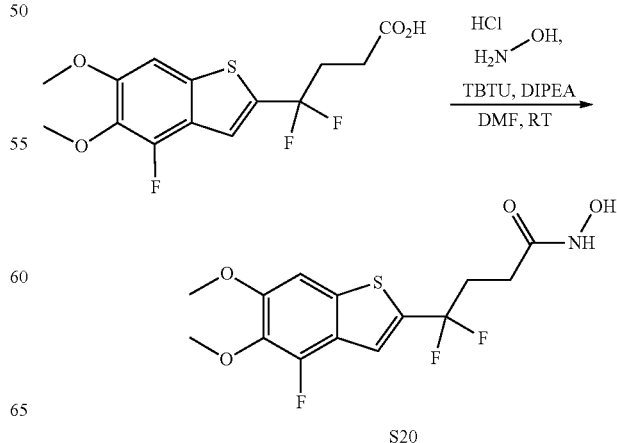

S20

Compound S19 (1 eq) was dissolved in N, N-dimethylformamide, and then hydroxylamine hydrochloride (1.0 eq), condensing agent TBTU (3 eq), and N,N-diisopropylethylamine (5 eq) were added sequentially, and reacted overnight at room temperature. After the reaction was completed, the reaction solution was poured into ice water, extracted with ethyl acetate, and the organic phase was collected and purified by column to obtain compound S20. $^1$H NMR (400 MHz, CDCl$_3$+CD$_3$OD) δ 8.19 (s, 1H), 7.58 (s, 1H), 3.98 (s, 3H), 3.93 (s, 3H), 2.88-2.62 (m, 4H), MS(EI): 349.

21. Synthesis of Compound S20

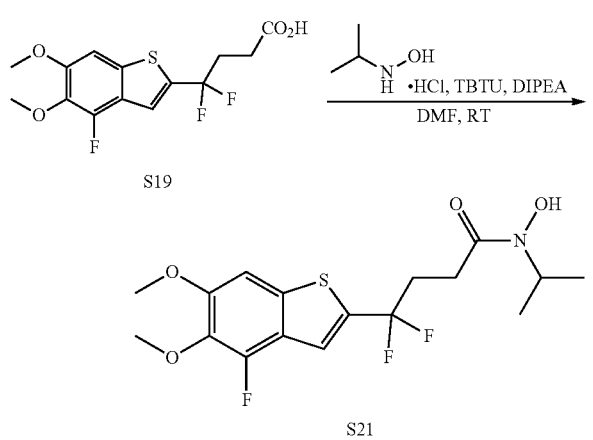

Compound S19 (1 eq) was dissolved in N, N-dimethylformamide, and then N-isopropylhydroxylamine hydrochloride (1.5 eq), TBTU (3 eq), and N,N-diisopropylethylamine (5 eq) were added sequentially, and reacted overnight at room temperature. After the reaction was completed, the reaction solution was poured into ice water, extracted with ethyl acetate, and the organic phase was collected and purified by column to obtain compound S21. $^1$H NMR (400 MHz, CDCl$_3$) δ7 $^1$H NMR (400 MHz, CDCl$_3$) δ 8.25 (s, 1H), 7.61 (s, 1H), 3.99 (s, 3H), 3.97 (s, 3H), 3.34 (m, 1H), 2.93-2.89 (m, 4H), 1.13 (d, J=4.0 Hz, 6H); MS (EI): 391.

22. Synthesis of Compound S22

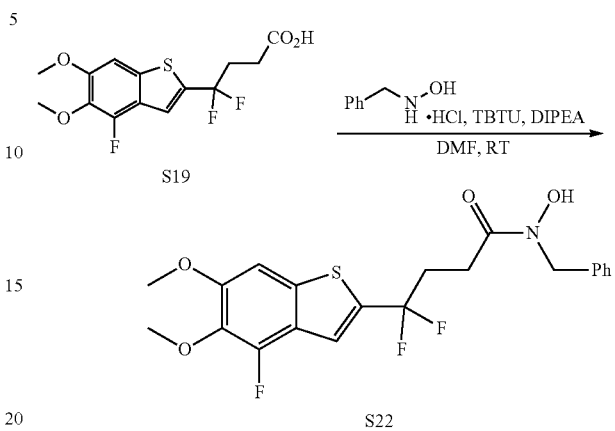

Compound S19 (I eq) was dissolved in N, N-dimethylformamide, and then N-benzylhydroxylamine hydrochloride (1.5 eq), TBTU (3 eq), and N,N-diisopropylethylamine (5 eq) were added sequentially, and reacted overnight at room temperature. After the reaction was completed, the reaction solution was poured into ice water, extracted with ethyl acetate, and the organic phase was collected and purified by column to obtain compound S22. $^1$H NMR (400 MHz, CDCl$_3$) δ $^1$H NMR (400 MHz, CDCl$_3$) δ 8.25 (s, 1H), 7.61 (s, 1H), 3.99 (s, 3H), 3.97 (s, 3H), 2.78 (m, 4H); MS (EI): 439.

23. Synthesis of Compound S23

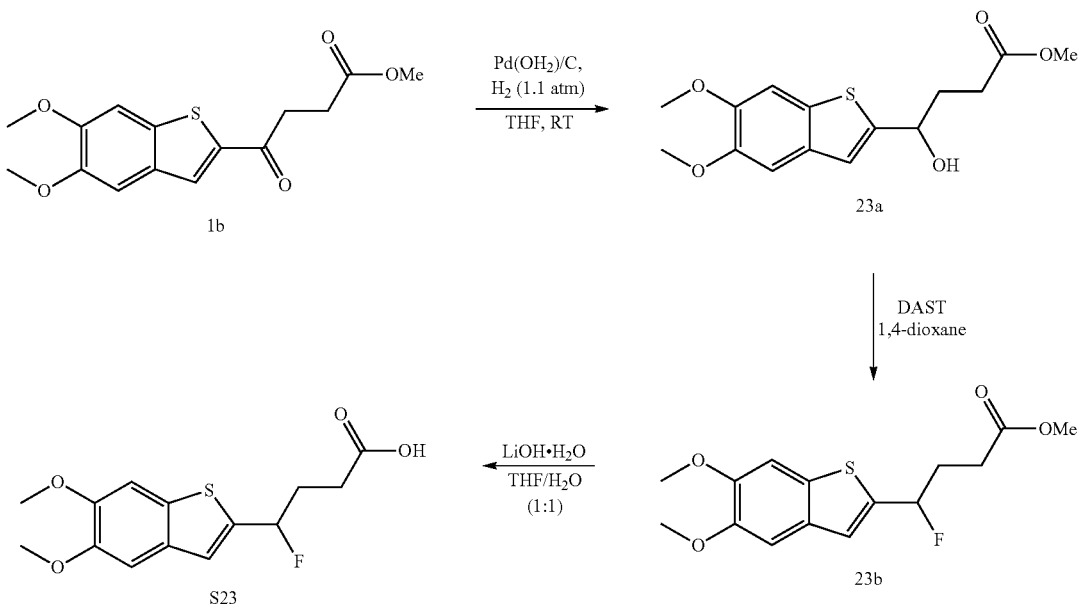

Step 1: compound 1b (1 eq) was suspended in methanol, followed by palladium hydroxide/carbon (20%), and reacted for 6 hours at 1.1 atm hydrogen environment at room temperature. After the reaction was completed, the reaction solution was filtered with diatomite, spin-dried, and purified by column to obtain compound 23a.

Step 2: Compound 23a (1 eq) was dissolved in dichloromethane. DAST (5 eq) was added under ice bath, after about 10 minutes, warmed to room temperature and reacted for two hours, after the reaction was completed, quenched with saturated sodium bicarbonate solution under ice bath, extracted with ethyl acetate, separated and purified by column to obtain compound 23b. $^1$H NMR (400 MHz, CDCl$_3$) δ 7.23 (s, 1H), 7.14 (s, 1H), 7.08 (s, 1H), 5.06 (t, J=6.7 Hz, 1H), 3.96 (s, 3H), 3.94 (s, 3H), 3.80 (s, 3H), 2.55 (s, 2H), 2.21 (d, J=6.5 Hz, 2H);

Step 3: compound 23b (1 eq) was dissolved in a mixed solvent of tetrahydrofuran:water (1:1), and then lithium hydroxide monohydrate (3 eq) was added, and reacted for half an hour at room temperature, the pH was adjusted to be 5-6 with 1N hydrochloric acid, extracted with chloroform, the organic phase was collected and purified by column to obtain compound S23. $^1$H NMR (400 MHz, CDCl$_3$) δ 7.75 (s, 1H), 7.31 (s, 1H), 7.16 (s, 1H), 5.16 (m, 1H), 3.99 (s, 3H), 3.96 (s, 3H), 2.55 (brs, 2H), 2.23 (d, J=6.5 Hz, 2H); MS (EI): 298

24. Synthesis of Compound S24 ride (1.5 eq), TBTU (3 eq), and N,N-diisopropylethyl amine (5 eq) were added sequentially, reacted overnight at room temperature. After the reaction was completed, the reaction solution was poured into ice water, extracted with ethyl acetate, and the organic phase was collected and purified by column to obtain compound S24. $^1$H NMR (400 MHz, CDCl$_3$) δ7.72 (s, 1H), 7.30 (brs, 1H), 7.21 (s, 1H), 7.18 (s, 1H), 5.24 (m, 1H), 3.98 (s, 3H), 3.96 (s, 3H), 3.23 (m, 1H), 2.57 (brs, 2H), 2.29 (d, J=6.5 Hz, 2H), 1.08 (d, 6H, J=4.0 Hz). MS (EI): 355.

25. Synthesis of Compound S25

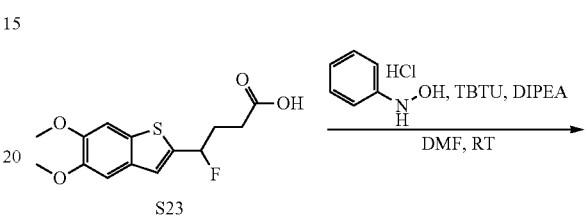

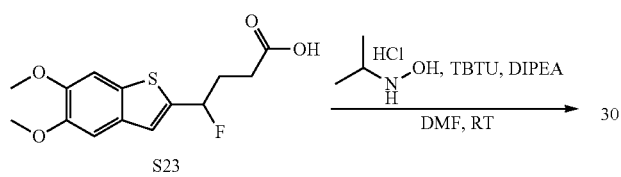

Compound S23 (1 eq) was dissolved in N, N-dimethylformamide, and then N-isopropylhydroxylamine hydrochlo- Compound S23 (1 eq) was dissolved in N, N-dimethylformamide, and then N-phenylhydroxylamine hydrochloride (1.5 eq), TBTU (3 eq), and N,N-diisopropylethylamine (5 eq) were added sequentially, and reacted overnight at room temperature. After the reaction was completed, the reaction solution was poured into ice water, extracted with ethyl acetate, and the organic phase was collected and purified by column to obtain compound S25. $^1$H NMR (400 MHz, CDCl$_3$) δ 8.23 (s, 1H), 7.62-7.53 (m, 5H), 7.35 (s, 1H), 7.31 (s, 1H), 5.31 (m, 1H), 3.98 (s, 3H), 3.97 (s, 3H), 2.49 (brs, 2H), 2.35 (d, J=6.5 Hz, 2H); MS (EI): 389.

26. Synthesis of Compound S26

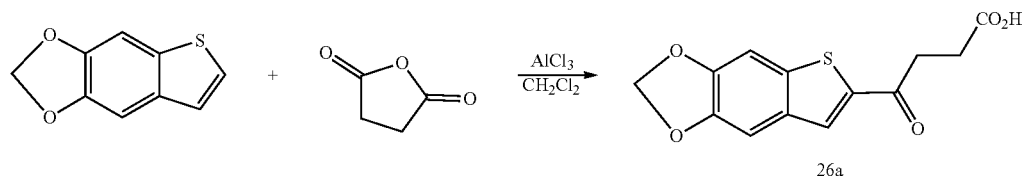

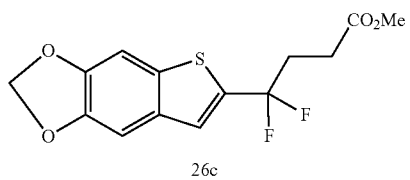

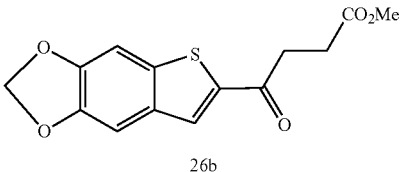

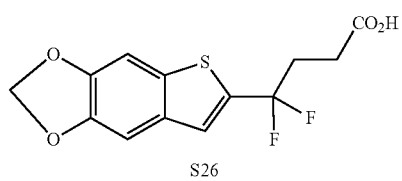

Step 1: succinic anhydride (1 eq) and aluminum trichloride (1.5 eq) were weighed out and dissolved in 1,2-dichloroethane, stirred at −10° C.; methylenedioxybenzo[b]thiophene (1.1 eq) was dissolved in 1,2-dichloroethane, which was dropped into the above reaction solution dropwise for 30 min. After dropping, continued to stir for 10 min and then transferred to a 45° C. oil bath, and reacted overnight. TLC was used to monitor the completion of the reaction, then the reaction solution was poured into ice water, 15% hydrochloric acid solution was added, stirred to precipitate the product, and filtered with suction to obtain the crude product. After dichloromethane recrystallization, pure product 26a was obtained. $^1$H NMR (400 MHz, DMSO) δ 11.98 (s, 1H), 8.04 (s, 1H), 7.43 (s, 1H), 7.36 (s, 1H), 5.95 (s, 2H), 3.23 (t, t, J=6.4 Hz, 2H), 2.51 (t, J=6.4 Hz, 2H).

Step 2: compound 26a (1 eq) was dissolved in methanol, and chlorinated sulfoxide (5 eq) was added dropwise at 0° C., and then moved to room temperature to react for 4 hours. After the reaction was completed, the solvent was spin-dried, and a small amount of water was added and the pH was adjusted to about 8 with saturated sodium bicarbonate solution, extracted with ethyl acetate, and the organic phase was collected and purified by column to obtain compound 26b;

Step 3: compound 26b (1 eq) was dissolved in dichloromethane, and DAST (5 eq) was added under an ice bath, after about 10 minutes, the temperature was warmed to 45° C., reacted for two hours, after the reaction solution was cooled to room temperature, quenched with saturated sodium bicarbonate solution under ice bath, extracted with ethyl acetate, separated and purified by column to obtain compound 26c. $^1$H NMR (400 MHz, CDCl$_3$) δ 7.32 (s, 1H), 7.21 (s, 1H), 7.14 (s, 1H), 5.87 (s, 2H), 3.64 (s, 3H), 2.64-2.57 (m, 4H); MS (EI): 314.

Step 4: Compound 26c (1 eq) was dissolved in a mixed solvent of tetrahydrofuran:water (1:1), and then lithium hydroxide monohydrate (3 eq) was added, and reacted for half an hour at room temperature, and the pH was adjusted to be 5-6 with 1N hydrochloric acid, extracted with chloroform, and the organic phase was collected and purified by column to obtain compound S26. $^1$H NMR (400 MHz, CDCl$_3$) δ 7.31 (s, 1H), 7.22 (s, 1H), 7.18 (s, 1H), 5.83 (s, 2H), 2.72-263 (m, 4H); MS (EI): 300.

27. Synthesis of Compound S27

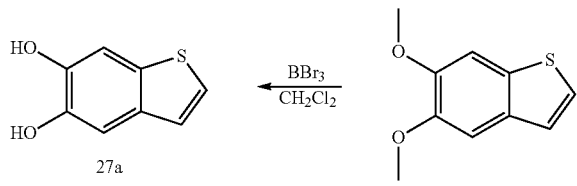

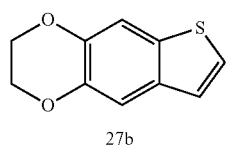 + 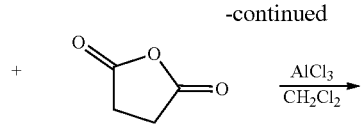 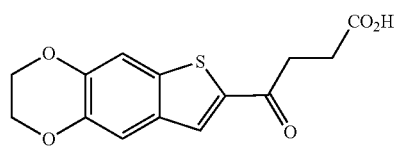

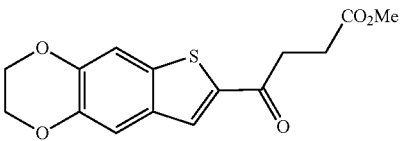

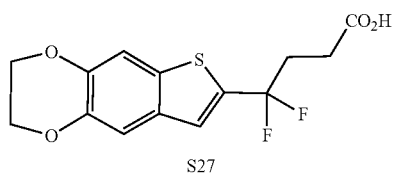

Step 1: compound 5,6-dimethoxybenzene [b]thiophene (1 eq) was dissolved in dichloromethane, a solution of 1.0 M boron tribromide in dichloromethane (6 eq) at −78° C. was added slowly and reacted for half an hour at −78° C., then moved to room temperature and reacted for about half an hour. After the reaction was completed, water was slowly added dropwise to quench under ice bath, and then extracted with dichloromethane, and purified by column to obtain intermediate 27a. 27a (1 eq) was dissolved in N, N-dimethylformamide, and 1,2-dibromoethane (1 eq) and potassium carbonate (4.5 eq) were added sequentially, and reacted overnight at 90° C. After cooling to room temperature, poured into ice water, extracted with ethyl acetate and purified by column to obtain compound 27b.

Step 2: succinic anhydride (1 eq) and aluminum trichloride (1.5 eq) were weighed out and dissolved in 1,2-dichloroethane, stirred at −10° C.; 27b (1.1 eq1) was dissolved in 1,2-dichloroethanewhich was added into the above reaction solution dropwise for 30 minutes. After the dropping, continued to stir for 10 minutes and then transferred to a 45° C. oil bath, and reacted overnight. TLC was used to monitor the completion of the reaction, then the reaction solution was poured into ice water, 15% hydrochloric acid solution was added, stirred to precipitate the product, and filtered with suction to obtain the crude product. The pure product 27c was obtained after recrystallization from dichloromethane.

Step 3: compound 27c (1 eq) was dissolved in methanol, and chlorinated sulfoxide (5 eq) was added dropwise at 0° C., and then moved to room temperature, reacted for 4 hours. After the reaction was completed, the solvent was spin-dried, and a small amount of water was added and the pH was adjusted to about 8 with saturated sodium bicarbonate solution, extracted with ethyl acetate, and the organic phase was collected and purified by column to obtain compound 27d;

Step 4: compound 27d (1 eq) was dissolved in dichloromethane, and DAST (5 eq) was added under an ice bath, after about 10 minutes, the temperature was warmed to 45° C., and reacted for two hours, after the reaction solution was cooled to room temperature, quenched with saturated sodium bicarbonate solution under ice bath, extracted with ethyl acetate, separated and purified by column to obtain compound 27e. $^1$H NMR (400 MHz, CDCl$_3$) δ 7.35 (s, 1H), 7.23 (s, 1H), 7.17 (s, 1H), 4.32 (m, 4H), 3.64 (s, 3H), 2.63-2.57 (m, 4H); MS (EI): 3280

Step 5: compound 27e (1 eq) was dissolved in a mixed solvent of tetrahydrofuran:water (1:1), and then lithium hydroxide monohydrate (3 eq) was added, reacted for half an hour at room temperature, and the pH was adjusted to be 5-6 with 1N hydrochloric acid, extracted with chloroform, the organic phase was collected and purified by column to obtain compound S27. $^1$H NMR (400 MHz, CDCl$_3$) δ 7.38 (s, 1H), 7.28 (s, 1H), 7.20 (s, 1H), 4.36 (m, 4H), 2.61-2.56 (m, 4H); MS (EI): 314.

28. Synthesis of Compound S28

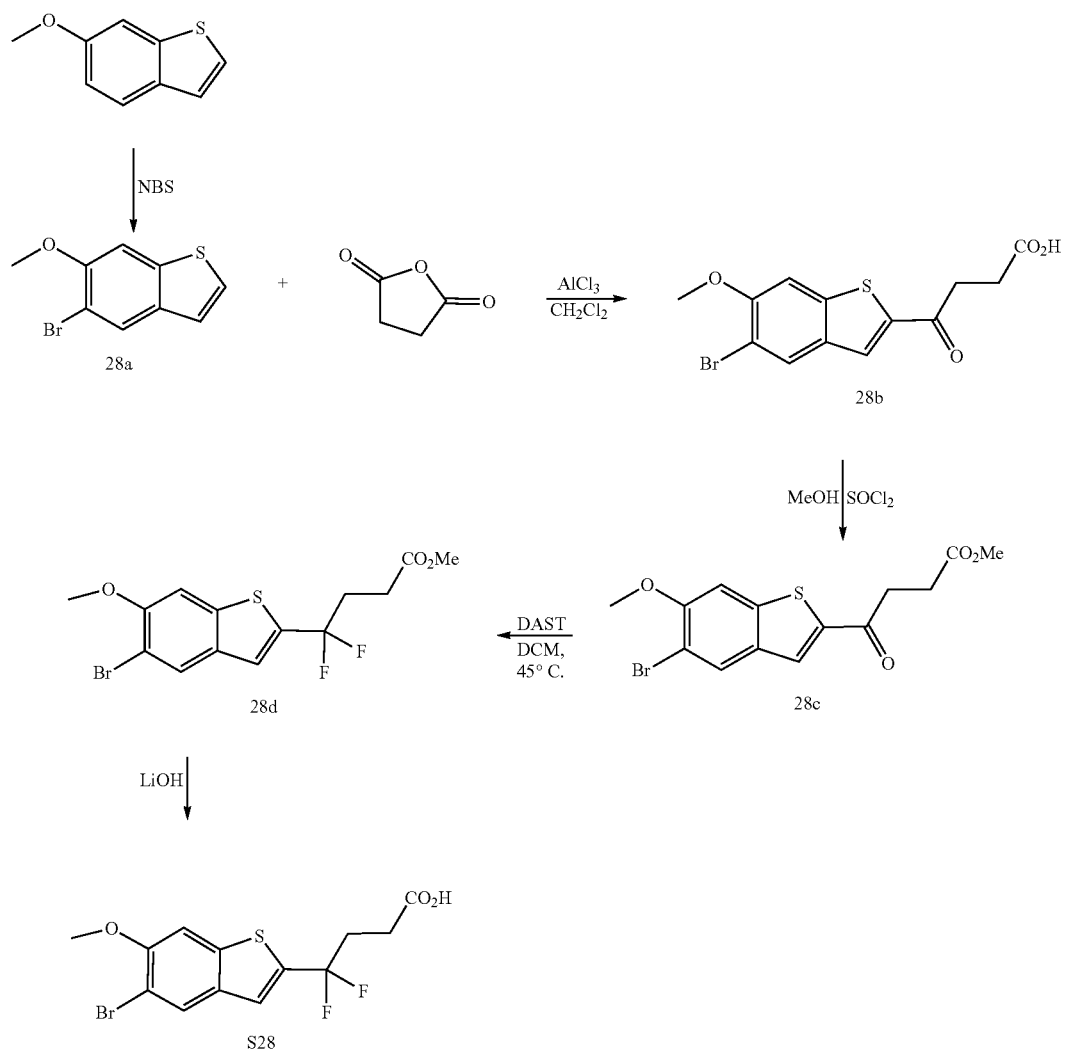

step 1: 6-methoxybenzothiophene (1 eq) was dissolved in dichloromethane, and NBS (1.1 eq) was added, and the reaction mixture was stirred for 6 hours. TLC was used to monitor the completion of the reaction, then the solvent was spun off and purified by column to obtain compound 28a.

Step 2: succinic anhydride (1 eq) and aluminum trichloride (1.5 eq) were weighed out and dissolved in 1,2-dichloroethane, and stirred at −10° C. 28a (1.1 eq) was dissolved in 1,2-dichloroethane, which was dropped into the above reaction solution dropwise for 30 min. After dripping, continued to stir for 10 min and then transferred to a 45° C. oil bath, and reacted overnight. TLC was used to monitor the completion of the reaction, then the reaction solution was poured into ice water, 15% hydrochloric acid solution was added, stirred to precipitate the product, and filtered with suction to obtain the crude product. The pure product 28b was obtained after recrystallization from dichloromethane.

Step 3: compound 28b (1 eq) was dissolved in methanol, and chlorinated sulfoxide (5 eq) was added dropwise at 0° C., and then moved to room temperature, and reacted for 4 hours. After the reaction was completed, the solvent was spin-dried, and a small amount of water was added and the pH was adjusted to about 8 with saturated sodium bicarbonate solution, extracted with ethyl acetate, and the organic phase was collected and purified by column to obtain compound 28c;

Step 4: compound 28c (0 eq) was dissolved in dichloromethane, and DAST (5 eq) was added under an ice bath, after about 10 minutes, the temperature was warmed to 45° C., and reacted for two hours, after the reaction solution was cooled to room temperature, quenched with saturated sodium bicarbonate solution under ice bath, extracted with ethyl acetate, separated and purified by column to obtain compound 28d. $^1$H NMR (400 MHz, CDCl$_3$) δ 7.81 (s, 1H), 7.36 (s, 1H), 7.22 (s, 1H), 3.94 (s, 3H), 3.64 (s, 3H), 2.61-2.54 (m, 4H).

Step 5: compound 28d (1 eq) was dissolved in a mixed solvent of tetrahydrofuran:water (1:1), and then lithium hydroxide monohydrate (3 eq) was added, and reacted for half an hour at room temperature, and the pH was adjusted to be 5-6 with 1N hydrochloric acid, extracted with chloroform, and the organic phase was collected and purified by column to obtain compound S28. $^1$H NMR (400 MHz, CDCl$_3$) δ 7.83 (s, 1H), 7.38 (s, 1H), 7.22 (s, 1H), 3.99 (s, 3H), 2.62-2.53 (m, 4H); MS (EI): 363.

29. Synthesis of Compound S29

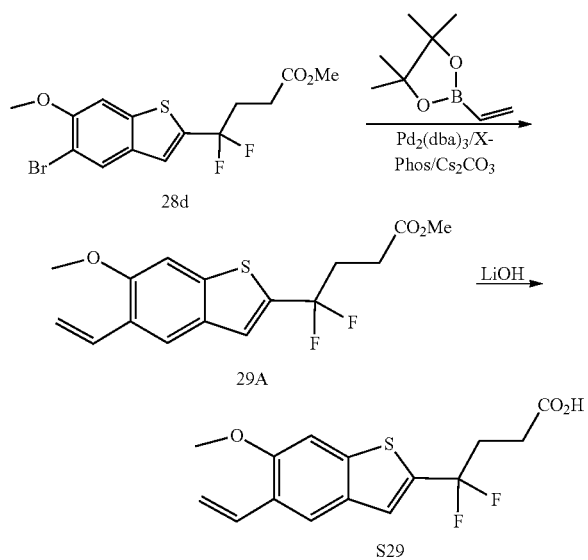

Step 1: 28d (1 eq), alkenyl borate (1.1 eq), catalyst Pd$_2$(dba)$_3$ (0.05 eq), ligand X-Phos (0.05 eq) and CS2CO3 (1 eq) were dissolved in dried toluene, and reacted for 12 hours at 110° C. TLC was used to monitor the completion of the reaction, then diluted with ethyl acetate, washed with saturated brine, the organic phase was dried over anhydrous Na2SO4, concentrated under reduced pressure and purified by column to obtain compound 29a. $^1$H NMR (400 MHz, CDCl$_3$) δ 7.56 (s, 1H), 7.30 (s, 1H), 7.18 (s, 1H), 6.52 (m, 1H), 5.30-5.48 (m, 2H), 3.96 (s, 3H), 3.61 (s, 3H), 2.65-2.58 (m, 4H);

step 2: compound 29a (1 eq) was dissolved in a mixed solvent of tetrahydrofuran:water (1:1), and then lithium hydroxide monohydrate (3 eq) was added, and reacted for half an hour at room temperature, and the pH was adjusted to be 5-6 with 1N hydrochloric acid, extracted with chloroform, the organic phase was collected and purified by column to obtain compound S29. $^1$H NMR (400 MHz, CDCl$_3$) δ 7.55 (s, 1H), 7.32 (s, 1H), 7.20 (s, 1H), 6.49 (m, 1H), 5.25-5.43 (m, 2H), 3.95 (s, 3H), 2.60-2.54 (m, 4H); MS (EI): 312.

30. Synthesis of Compound S30

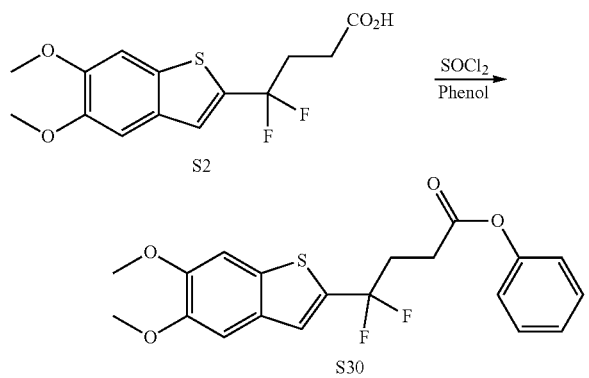

Compound S2 (1 eq) was dissolved in 1,4-dioxane, and then chlorinated sulfoxide (5 eq) was added dropwise at 0° C., and then phenol (1.1 eq) was added, after the reaction was completed, moved to room temperature to react for 4 hours. After the reaction was completed, the solvent was spin-dried, and a small amount of water was added and the pH was adjusted to about 8 with saturated sodium bicarbonate solution, extracted with ethyl acetate, and the organic phase was collected and purified by column to obtain compound S30. $^1$H NMR (400 MHz, CDCl$_3$) δ 7.82 (s, 1H), 7.19 (s, 1H), 7.430-7.39 (m, 5H), 7.19 (s, 1H), 3.97 (s, 3H), 3.94 (s, 3H), 2.79-2.68 (m, 4H); MS (EI): 358.

31. Synthesis of Compound S31

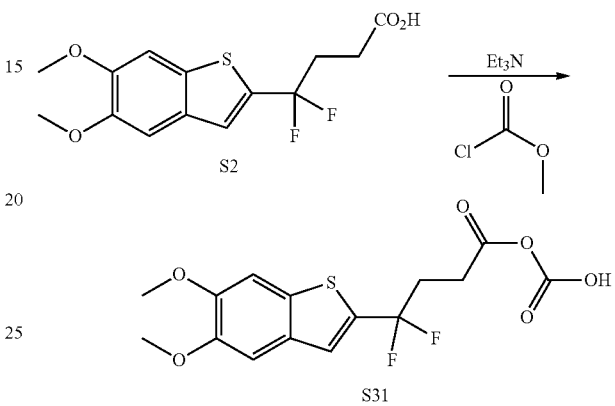

Compound S2 (1 eq) was dissolved in 1,4-dioxane, and methyl chloroformate (3 eq) was added dropwise at 0° C. and then Et3N (2 eq) was added, after the reaction was completed, moved to room temperature to react for 12 hours. After the reaction was completed, the solvent was spin-dried, a small amount of water was added, extracted with ethyl acetate, the organic phase was collected and purified by column to obtain compound S31. $^1$H NMR (400 MHz, DMSO-d6) δ 11.18 (brs, 1H), 7.39 (s, 1H), 7.28 (s, 1H), 7.22 (s, 1H), 3.96 (s, 3H), 3.94 (s, 3H), 2.70-2.58 (m, 4H); MS (EI): 360.

32. Synthesis of Compound S32

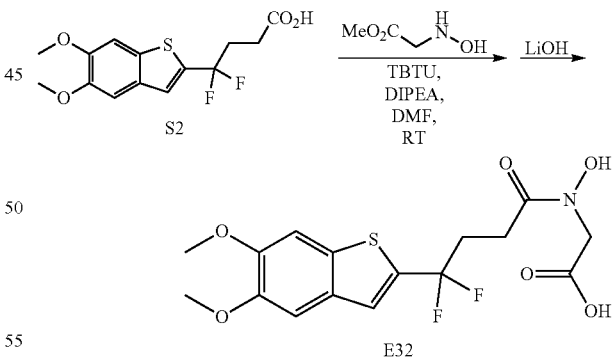

Compound S2 (1 eq) was dissolved in N, N-dimethylformamide, and then N-methyl acetate hydroxylamine hydrochloride (1.5 eq), TBTU (3 eq), and N,N-diisopropylethylamine (5 eq) were added sequentially, and reacted overnight at room temperature. After the reaction was completed, the reaction solution was poured into ice water, extracted with ethyl acetate, the organic phase was collected and purified by column to obtain an intermediate: the intermediate (1 eq) was dissolved in a mixed solvent of tetrahydrofuran:water (1:1), and then lithium hydroxide monohydrate (3 eq) was added, reacted at room temperature for half an hour, the pH was adjusted to be 5-6 with 1N hydrochloric acid, extracted with chloroform, and collected the organic phase, purified by column to obtain compound S32. $^1$H NMR (400 MHz, CDCl$_3$) δ 7.40 (s, 1H), 7.29 (s, 1H), 7.22 (s, 1H), 4.13 (s, 2H), 3.99 (s, 3H), 3.97 (s, 3H), 2.72-2.65 (m, 4H); MS (EI): 389.

33. Synthesis of Compound S33

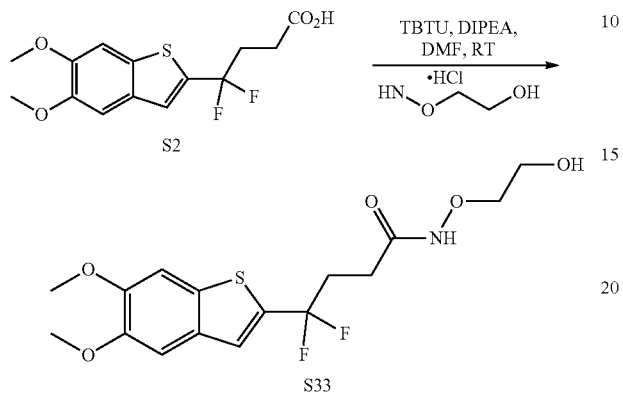

Compound S2 (1 eq) was dissolved in N, N-dimethylformamide, and then O-hydroxyethylhydroxylamine hydrochloride (1.5 eq), TBTU (3 eq), and N,N-diisopropylethylamine (5 eq) were added sequentially, and reacted overnight at room temperature. After the reaction was completed, the reaction solution was poured into ice water, extracted with ethyl acetate, and the organic phase was collected and purified by column to obtain compound S33. $^1$H NMR (400 MHz, CDCl$_3$) δ 7.88 (s, 1H), 7.32 (s, 1H), 7.28 (s, 1H), 3.97 (s, 3H), 3.96 (s, 3H), 3.72 (t, 2H, J=8.4 Hz), 3.54 (t, 2H. J=8.0 Hz), 2.84-2.65 (m, 4H). MS (EI): 375.

II. Cell Screening Experiment for the Compound to Activate the Interferon Gene Stimulating Protein and Promote the Expression of IFN-β

Detection method and principle: Human-derived THP1-Blue-ISG cells were transferred with a reporter system containing IFN-β, which could induce the expression of downstream alkaline phosphatase. When alkaline phosphatase was secreted extracellular, OD650 was measured by color reaction to reflect the content. When the compound was added to the cell, if the interferon gene stimulating protein was activated, then the expression of IFN-β could be promoted, thereby the secretion of downstream alkaline phosphorylation and the absorbance of the color reaction could be increased.

Experiment Method:
1. Addition of compound: 20 μL of compound diluted with saline was added to each well of 96-well cell culture plate.

The concentration of the compound was 100 μM, 2 duplicate holes were set. The positive control compound was ADU-S100 with the concentration of 100 μM. The untreated control group was given 20 μL of normal saline containing 1% DMSO.

2. Addition of cells: THP1-Blue-ISG cell was counted, adjusted cell concentration to be 5×10$^5$/mL, and 180 μl of cells were added to each well for incubation. Therefore, each test hole had a final volume of 200 μL, and the content of DMSO was 0.1%, and the test concentration of the compound was 10 μM. The final concentration of the positive control compound ADU-S100 was 10 μM, incubated for 24 hours for detection.

The blank control group was added with 180 μL medium solution.

3. Detection of the color reaction: After 24 hours, 20 μL of medium solution was taken from each well to a new 96-well plate, 200 μL of color development solution Quanti-Blue was added, placed in a 37° C. incubator, and the OD650 value was measured after 0.5-2 hours.
4. Screening concentration of the compound: 10 μM.
5. Result analysis:

$$\text{Fold Change} = \frac{(\text{Compound } OD650 - \text{Blank } OD650)}{(\text{Control } OD650 - \text{Blank } OD650)}$$

where Compound OD650 is an OD650 value of the compound of the present invention, BLANK OD650 is the OD650 value of the medium, and Control OD650 is an OD650 value of the control group without the compound (only cells and 0.1% DMSO).

6. Result judgement: when the Fold change≥2, it is effective.

Experimental Results:

TABLE 2 the ability of some compounds to activate human-derived interferon gene stimulating protein in THP1 cells at a concentration of 10 μM to promote the expression of type I interferon

| Compound (10 μM) | Fold change (ratio relative to the control experiment) | | | |
|---|---|---|---|---|
| | First experiment | Second experiment | Average value | Judgement |
| S1 | 24.20 | 33.38 | 28.79 | effective |
| S2 | 23.95 | 25.94 | 24.95 | effective |
| S3 | 24.31 | 33.69 | 29.00 | effective |
| S6 | 15.82 | 26.22 | 21.02 | effective |
| S7 | 23.95 | 29.94 | 26.95 | effective |
| S10 | 25.41 | 34.36 | 29.89 | effective |
| S11 | 20.44 | 30.93 | 25.69 | effective |
| S12 | 22.38 | 31.54 | 26.96 | effective |
| S15 | 26.23 | 35.12 | 30.68 | effective |
| S18 | 17.62 | 28.34 | 22.98 | effective |
| S19 | 25.73 | 31.81 | 28.77 | effective |
| S21 | 27.51 | 32.63 | 30.07 | effective |
| S24 | 15.53 | 24.54 | 20.04 | effective |
| S26 | 16.24 | 25.03 | 20.62 | effective |
| S28 | 23.75 | 33.73 | 28.74 | effective |
| S29 | 25.26 | 34.05 | 29.66 | effective |
| 1a | 13.80 | 10.52 | 12.16 | effective |
| ADU-S100 | 21.52 | 31.47 | 26.50 | effective |
| CON | 1.00 | 1.00 | 1.00 | |

Among them, CON represents a control without the compound (i.e., only cells and 0.1% DMSO).

The above results showed that at a concentration of 10 uM, the tested compounds can significantly activate the interferon gene stimulating protein and promote the expression of interferon factor IFN-β. Among them, the agonistic activity of most of the compounds is comparable to or even better than the phase I clinical cyclic dinucleoside compound ADU-S100, and has further application prospects.

In addition, compared to compound 1a (that is, compound 16 in the published patent) disclosed in TW201817723A (US20180093964), compounds S1-3, S7, S1, S11-12, S15, S19, S21, S28-29 have 2-2.5 times enhanced agonistic activity.

III. Study on the Drug Metabolism Properties of Compound S2

TABLE 3

Comparison of pharmacokinetic properties of compound S2 and 1a in rats

| Mode of administration | Compound number | $T_{1/2}$ (h) | $C_{max}$ (ng/mL) | AUC (h*ng/mL) | CL (mL/min/kg) | MRT (h) |
|---|---|---|---|---|---|---|
| Oral (3 mg/kg) | 1a | 0.656 | 5171 | 3424 | — | 0.854 |
|  | S2 | 0.740 | 6906 | 5818 | — | 1.15 |
| Intravenous (1 mg/kg) | 1a | 0.471 | — | 1649 | 10.3 | 0.510 |
|  | S2 | 0.669 | — | 7180 | 2.33 | 0.853 |

The above data showed that whether the representative compound S2 described in this patent was administered orally or intravenously, its half-life ($T_{1/2}$), maximum plasma solubility (Cmax), plasma exposure (AUC) and mean residence time (MRT) and other indicators were significantly better than compound 1a (that is, compound 16 in the published patent) disclosed in TW201817723A (US20180093964), especially the AUC of intravenous injection, which was about 4.4 times of that of 1a, which was significantly improved.

All literatures mentioned in the present invention are incorporated by reference herein, as though individually incorporated by reference. Additionally, it should be understood that after reading the above teaching, many variations and modifications may be made by the skilled in the art, and these equivalents also fall within the scope as defined by the appended claims.

The invention claimed is:
1. A compound of formula I, or its isomer, prodrug, solvate, hydrate or pharmaceutically acceptable salt thereof,

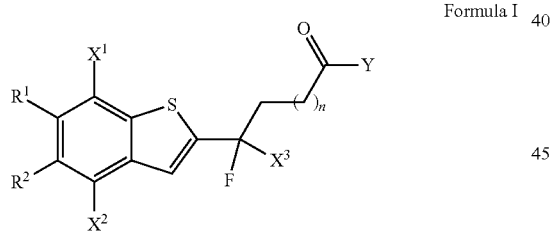

Formula I wherein,
$R^1$ and $R^2$ are independently selected from the substituted or unsubstituted group consisting of halogen, amino, hydroxyl, carboxyl, C1-C6 alkyl, C2-C6 alkenyl, C2-C6 alkynyl, C3-C8 cycloalkyl, C1-C6 alkoxy, C3-C8 cycloalkoxy, 3-8 membered heterocycloalkyl containing 1 to 3 heteroatoms selected from N, O or S, 3-8 membered heterocycloalkoxy containing 1 to 3 heteroatoms selected from N, O or S, C6-C10 aryl, and 3-10 membered heteroaryl containing 1 to 3 heteroatoms selected from N, O or S; or $R^1$ and $R^2$ together with the carbon atoms to which they are attached form a 5-14 membered heterocyclic group;
the substituted in $R^1$ and $R^2$ refers to be independently substituted by one or more substituents selected from the group consisting of halogen, amino, hydroxy, carboxy, C1-C6 alkyl, C3-C8 cycloalkyl, C1-C6 alkoxy, C3-C8 cycloalkoxy, 3-8 membered heterocyclic group containing 1 to 3 heteroatoms selected from N, O or S, C6-C10 aryl, and 3-10 membered heteroaryl containing 1 to 3 heteroatoms selected from N, O or S;

$X^1$ and $X^2$ are independently selected from the group consisting of H, D, halogen, unsubstituted or halogen-substituted C1-C6 alkyl, unsubstituted or halogen-substituted C1-C6 alkoxy, and cyano;

$X^3$ is selected from the group consisting of hydrogen, halogen, hydroxy, C1-C3 alkyl, C1-C3 alkoxy;

n is an integer selected from 0, 1, 2, 3, 4, 5, 6, 7 or 8;

Y is selected from the group consisting of —OR3, and —N($X^4R^4$) $R^5$, wherein, $X^4$ is selected from the group consisting of O, S, and NH;

$R^3$ is selected from the substituted or unsubstituted group consisting of H, carboxy, sulfonic acid group, phosphoryl group, C1-C6 alkyl, C3-C8 cycloalkyl, C6-C10 aryl, 3-10 membered heteroaryl containing 1 to 3 heteroatoms selected from N, O or S, and 3-8 membered heterocycloalkyl containing 1 to 3 heteroatoms selected from N, O or S;

$R^4$ and $R^5$ are independently selected from the substituted or unsubstituted group consisting of H, carboxy, sulfonic acid group, phosphoryl group, C1-C6 alkyl, C2-C6 alkenyl, C2-C6 alkynyl, C3-C8 cycloalkyl, C1-C6 alkoxy, C3-C8 cycloalkoxy, C6-C10 aryloxy, C6-C10 aryl, 3-8 membered heterocycloalkyl containing 1 to 3 heteroatoms selected from N, O or S, and 3-10 membered heteroaryl containing 1 to 3 heteroatoms selected from N, O or S;

the substituted in $R^3$, $R^4$ and $R^5$ refers to be independently substituted by one or more substituents selected from the group consisting of halogen, hydroxyl, amino, carboxyl, C1-C6 alkyl, C3-C8 cycloalkyl, C1-C6 alkoxy, C3-C8 cycloalkoxy, 3-8 membered heterocyclic group containing 1 to 3 heteroatoms selected from N, O or S, C6-C10 aryl, and 3-10 membered heteroaryl containing 1 to 3 heteroatoms selected from N, O or S.

2. The compound, or its isomer, prodrug, solvate, hydrate or pharmaceutically acceptable salt thereof according to claim 1, wherein $X^3$ is halogen.

3. The compound, or its isomer, prodrug, solvate, hydrate or pharmaceutically acceptable salt thereof according to claim 2, wherein $X^2$ is hydrogen or fluorine.

4. The compound, or its isomer, prodrug, solvate, hydrate or pharmaceutically acceptable salt thereof according to claim 1, wherein n is an integer selected from 0, 1 or 2.

5. The compound, or its isomer, prodrug, solvate, hydrate or pharmaceutically acceptable salt thereof according to claim 1, wherein Y is selected from the group consisting of —OR₃, and —N($X^4R^4$) $R^5$, wherein, $X^4$ is selected from the group consisting of: O, and NH.

6. The compound, or its isomer, prodrug, solvate, hydrate or pharmaceutically acceptable salt thereof according to claim 1, wherein the compound is selected from the group consisting of:

| Compound number | structure |
|---|---|
| S1 | 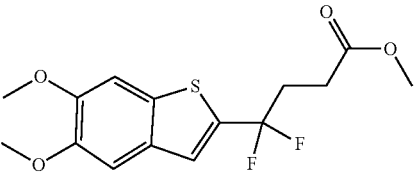 |
| S2 | 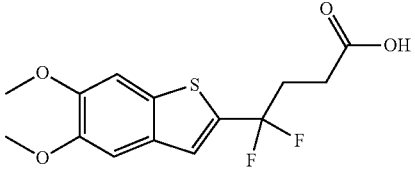 [SMILES: COc1cc2cc(C(F)(F)CCC(=O)O)sc2cc1OC] |
| S3 | 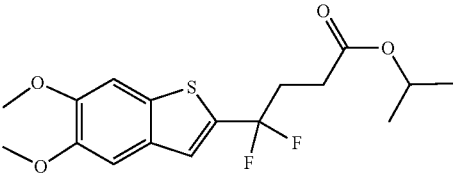 [SMILES: COc1cc2cc(C(F)(F)CCC(=O)OC(C)C)sc2cc1OC] |
| S4 | 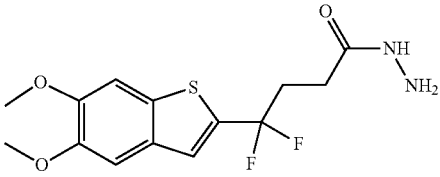 [SMILES: COc1cc2cc(C(F)(F)CCC(=O)NN)sc2cc1OC] |
| S5 | 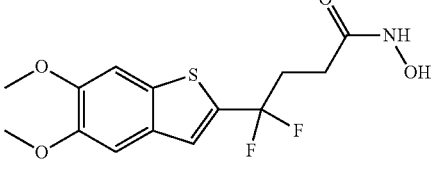 |
| S6 | 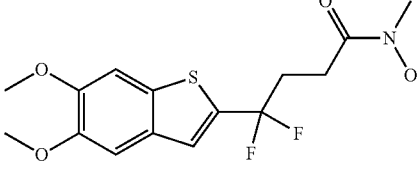 |
| S7 | 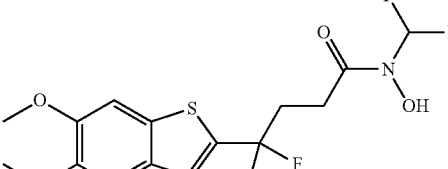 |
| S8 | 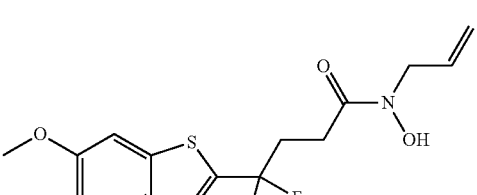 |

| Compound number | structure |
|---|---|
| S9 | 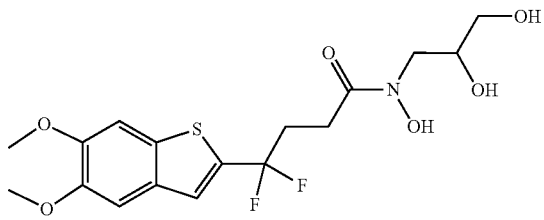 [SMILES: COc1cc2cc(C(F)(F)CCC(=O)N(O)CC(O)CO)sc2cc1OC] |
| S10 | 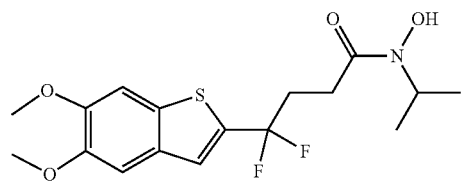 [SMILES: COc1cc2cc(C(F)(F)CCC(=O)N(O)C(C)C)sc2cc1OC] |
| S11 | 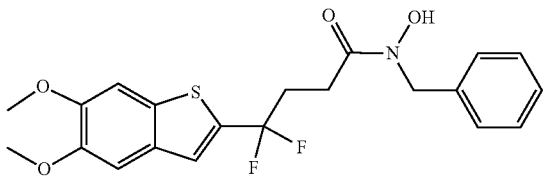 [SMILES: COc1cc2cc(C(F)(F)CCC(=O)N(O)Cc3ccccc3)sc2cc1OC] |
| S12 | 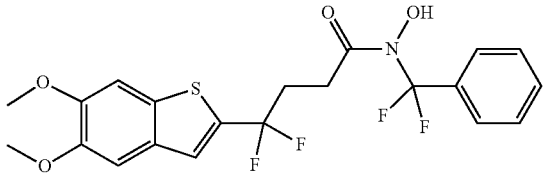 |
| S13 | 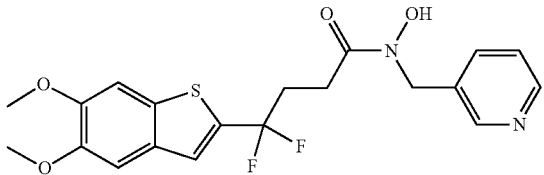 [SMILES: COc1cc2cc(C(F)(F)CCC(=O)N(O)Cc3cccnc3)sc2cc1OC] |
| S14 | 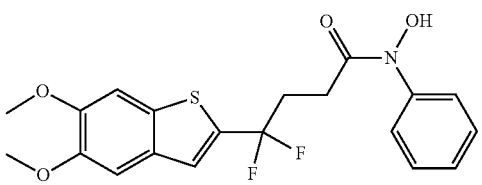 [SMILES: COc1cc2cc(C(F)(F)CCC(=O)N(O)c3ccccc3)sc2cc1OC] |
| S15 | 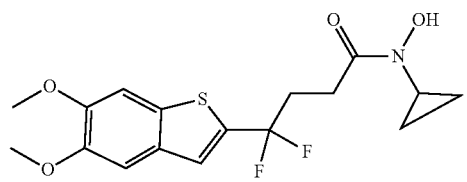 [SMILES: COc1cc2cc(C(F)(F)CCC(=O)N(O)C3CC3)sc2cc1OC] |

-continued
| Compound number | structure |
|---|---|
| S16 | 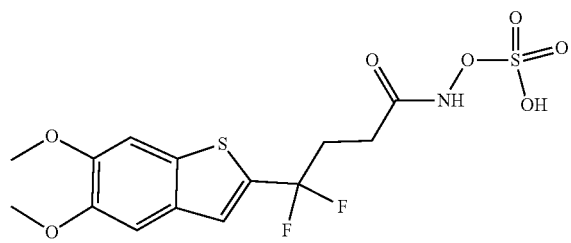 [SMILES: COc1cc2cc(C(F)(F)CCC(=O)NOS(=O)(=O)O)sc2cc1OC] |
| S17 | 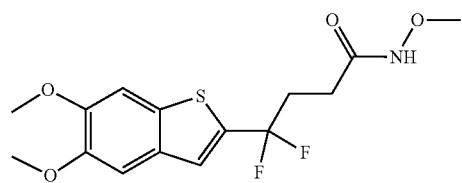 |
| S18 | 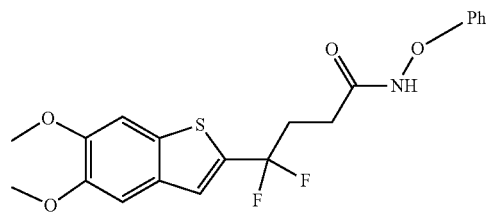 [SMILES: COc1cc2cc(C(F)(F)CCC(=O)NOc3ccccc3)sc2cc1OC] |
| S19 | 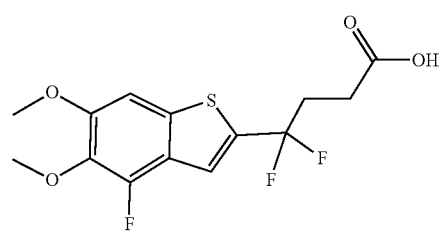 [SMILES: COc1cc2sc(C(F)(F)CCC(=O)O)cc2c(F)c1OC] |
| S20 | 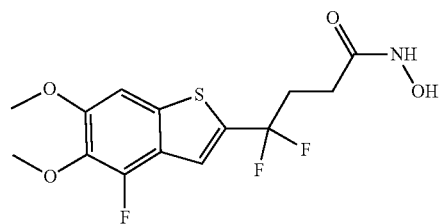 [SMILES: COc1cc2sc(C(F)(F)CCC(=O)NO)cc2c(F)c1OC] |
| S21 | 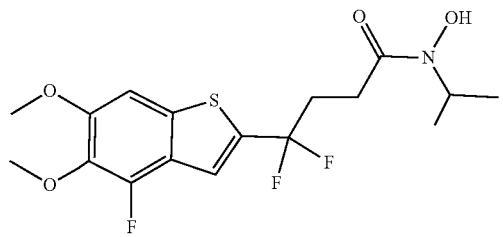 [SMILES: COCc1c(OC)cc2sc(C(F)(F)CCC(=O)N(O)C(C)C)cc2c1F] |

-continued

| Compound number | structure |
|---|---|
| S22 | ![structure] |
| S23 | ![structure] |
| S24 | ![structure] |
| S25 | ![structure] |
| S26 | ![structure] |
| S27 | ![structure] |
| S28 | ![structure] |
| S29 | ![structure] |

| Compound number | structure |
| --- | --- |
| S30 | 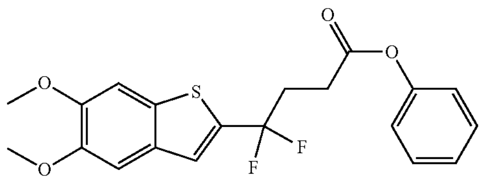 [SMILES: COc1cc2cc(C(F)(F)CCC(=O)Oc3ccccc3)sc2cc1OC] |
| S31 | 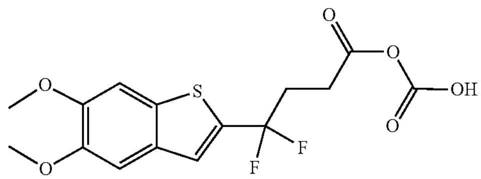 [SMILES: COc1cc2cc(C(F)(F)CCC(=O)OC(=O)O)sc2cc1OC] |
| S32 | 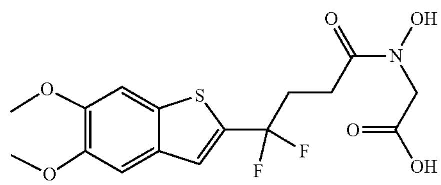 [SMILES: COc1cc2cc(C(F)(F)CCC(=O)N(O)CC(=O)O)sc2cc1OC] |
| S33 | 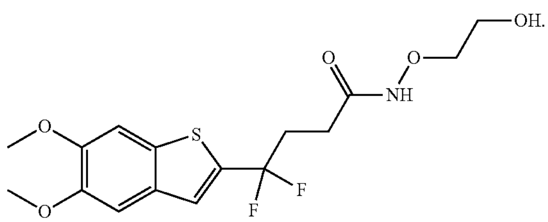 [SMILES: COc1cc2cc(C(F)(F)CCC(=O)NOCCO)sc2cc1OC] |

7. A method for preparing the compound, or its isomer, prodrug, solvate, hydrate, or pharmaceutically acceptable salt thereof according to claim 1, wherein the method is selected from the group consisting of:

Method 1:

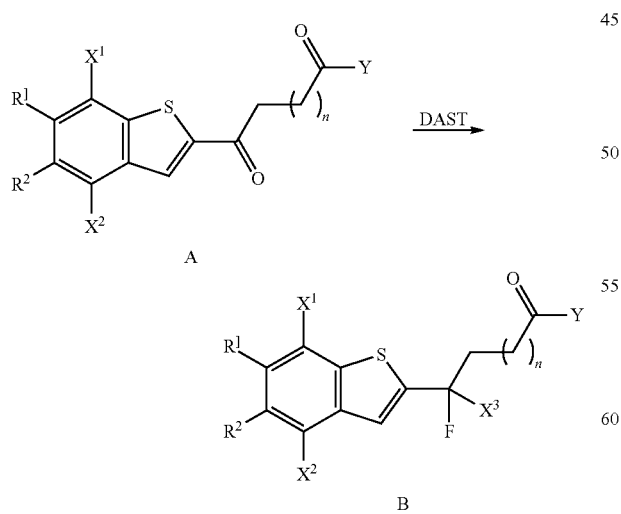

a compound of formula A is reacted with DAST to obtain B;

Method 2:

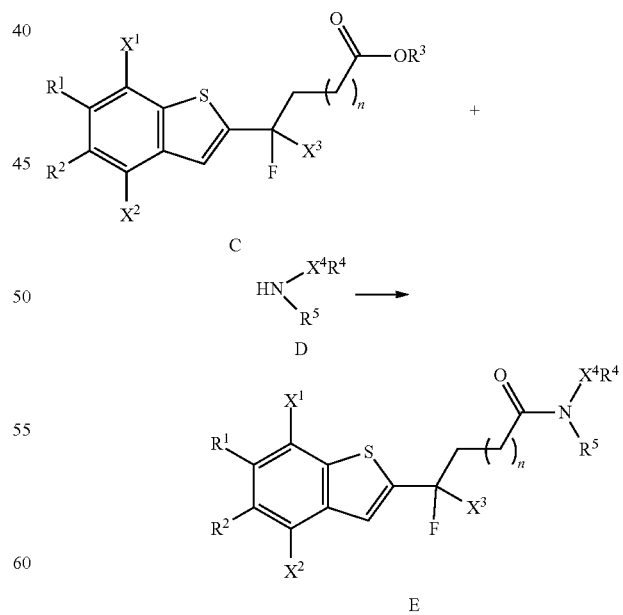

a compound of formula C is reacted with a compound of formula D or a hydrochloride thereof to obtain E, wherein.

8. A pharmaceutical composition comprising:
(i) one or more therapeutically effective amount of the compound, or its isomer, prodrug, solvate, hydrate or pharmaceutically acceptable salt thereof according to claim 1; and
ii) a pharmaceutically acceptable carrier.

9. A method for treating diseases related to type I interferon comprising the step of administrating the compound, or its isomer, prodrug, solvate, hydrate or pharmaceutically acceptable salt thereof according to claim 1 to a subject in need thereof.

10. An interferon gene stimulating protein agonist comprising one or more of the compound, or its isomer, prodrug, solvate, hydrate or pharmaceutically acceptable salt thereof according to claim 1.

* * * * *